US007846971B2

(12) United States Patent
Najafi et al.

(10) Patent No.: US 7,846,971 B2
(45) Date of Patent: Dec. 7, 2010

(54) N-HALOGENATED AMINO ACIDS, N,N-DIHALOGENATED AMINO ACIDS AND DERIVATIVES; COMPOSITIONS AND METHODS OF USING THEM

(75) Inventors: Ramin Najafi, Novato, CA (US); Mansour Bassiri, Albany, CA (US); Lu Wang, Moraga, CA (US); Behzad Khosrovi, El Cerrito, CA (US)

(73) Assignee: Novabay Pharmaceuticals, Inc., Emeryville, CA (US)

( * ) Notice: Subject to any disclaimer, the term of this patent is extended or adjusted under 35 U.S.C. 154(b) by 1315 days.

(21) Appl. No.: 11/339,987

(22) Filed: Jan. 25, 2006

(65) Prior Publication Data

US 2006/0247209 A1    Nov. 2, 2006

Related U.S. Application Data

(60) Provisional application No. 60/647,366, filed on Jan. 25, 2005.

(51) Int. Cl.
*A61K 31/13* (2006.01)
*C07C 309/18* (2006.01)
*C07C 309/13* (2006.01)
*C07C 309/14* (2006.01)

(52) U.S. Cl. .................. 514/612; 562/104; 562/105
(58) Field of Classification Search ................. 562/104, 562/105; 514/612
See application file for complete search history.

(56) References Cited

U.S. PATENT DOCUMENTS

| | | | |
|---|---|---|---|
| 3,950,536 A | 4/1976 | Barer et al. | |
| 3,966,796 A | 6/1976 | Kaminski et al. | |
| 3,998,945 A | 12/1976 | Vit et al. | ........................ 424/53 |
| 4,015,008 A | 3/1977 | Barer et al. | |
| 4,045,578 A | 8/1977 | Kaminski et al. | |
| 4,386,103 A | 5/1983 | Pogany et al. | |
| 5,096,700 A | 3/1992 | Seibel et al. | |
| 5,985,239 A | 11/1999 | Hussain et al. | |
| 6,451,761 B1 | 9/2002 | van Gelder | ..................... 514/2 |
| 7,129,259 B2 | 10/2006 | Chen et al. | |
| 2004/0022871 A1* | 2/2004 | Mainnemare | ................ 424/661 |
| 2005/0065115 A1 | 3/2005 | Bassiri et al. | |

FOREIGN PATENT DOCUMENTS

| | | | |
|---|---|---|---|
| DE | 4041703 | 7/1992 | |
| DE | 4041703 A1 | 7/1992 | .................. 309/14 |
| DE | 4041703 C2 | 7/1992 | .................. 309/14 |
| DE | 198 16 102 C1 | 9/1998 | |
| DE | 197 12 565 A1 | 10/1998 | |
| DE | 19712565 | 10/1998 | |
| DE | 19816102 | 9/1999 | |
| JP | 07206609 | 8/1995 | |
| WO | WO 02/22118 A1 | 3/2002 | .................. 31/185 |
| WO | 02058692 | 8/2002 | |
| WO | WO 02/058692 A2 | 8/2002 | |
| WO | WO 2005/020896 | 3/2005 | |
| WO | WO 2008/083347 | 7/2008 | |

OTHER PUBLICATIONS

Egawa, et al.; "Reactions of N,N-dichloroalkylamines with solid base as studied by FTIR combined with DFT calculations" J. Mol. Struct. (2001), 560(1-3):337-344.
Advances in Pharmaceutical Sciences vol. 7. (Eds., 1995).
Bozeman P. et al., "Oxidation of Bromide by the Human Leukocyte Enzymes Myeloperoxidase and Eosinophil Peroxidase", *J. Bio. Chem.*, 7, pp. 2906-2913, 1995.
Braghiroli, D. et al., "New Methods for the Preparation of 2-Amino-2-methylpropanesulfonic Acid", *Tetrahedron Letters*, vol. 37, pp. 7319-7322, 1996.
Brown, H.C.; "Organic Synthesis via Boranes", Wiley-Interscience: New York, 1975.
Chinake, et al., "Oxyhalogen-sulfur Chemistry: Kinetics and Mechanism of the Oxidation of a Bunte Salt 2-Aminoethanethiolsulfuric Acid by Chlorite", *Phys. Chem. Chem. Phys*; vol. 3: pp. 4957-4964, 2001.
Davies, et al., *Neurosci. Lett.* 21: pp. 77-81, 1981.
E. A. Boyd, M. et al., "A Versatile Route to Substituted Phosphinic Acids", Tetrahedron Lett., 1990, 31, 20, 2933-2936.
Evans, R.H. et al., "The Effects of a Series of ω-Phosphonic α-Carboxylic amino Acids on Electrically Evoked and Excitant Amino Acids-Induced Responses in Isolated Spinal Cord Preparations", Br. J. Pharmac., vol. 75, pp. 65-75, 1982.
G. M. Kosolapoff, The Synthesis of Phosphonic and Phosphinic Acids, Organic Reactions, vol. 6 (1951).
Gelder, N.M., et al., Synthesis and characterization of N,N-dichlorinated amino acids: Taurine, Homotaurine, GABA and L-Leucine; *J. Neurochemical Research*; 26: pp. 575-578 2001.
J Marcinkiewicz et al., *J of Inflammatory Research* 49, pp. 280-289 2000.
J. M. Antelo; F. Arce, J. Crugeiras, M. Parajó, "General acid-base catalysis in the reversible disproportionation reaction of N-chlorotaurine", *J. Chem. Soc. Perkin Trans.* 2, 2000, 2109-2114.
*J. Phys. Chem. A.* 1998; 102: pp. 9838-9846.
Kamatani, A., et al., *J. Org. Chem.* 1999, 64, pp. 8743-8744.
Lapenna D., et al., *Gen. Pharmacol.* Oct. 1996; 27(7): 1145-1147.
Mainnemare A, et al., Hypochlorous acid and taurine-N-monochloramine in periodontal disease; *J Dent Res.* 83 (11): pp. 823-831 (Nov. 2004).
*Medical Plastics and Biomaterials Magazine*, Mar. 1998, p. 30.
Merck Index, Thirteenth Edition, 2001, Entries 2084 and 2085 on p. 356.
Miyaura, N. and Suzuki, A. Chem. Rev. 1995, 95, pp. 2457-2483.
Nagl, M. *Arch. Pharm. Med. Chem.* 2002, 9, pp. 411-421.

(Continued)

*Primary Examiner*—Peter G. O'Sullivan
(74) *Attorney, Agent, or Firm*—Hamilton Desanctis & Cha LLP

(57) ABSTRACT

The present invention relates to active bactericidal, antibacterial, anti-infective, antimicrobial, sporicidal, disinfectant, antifungal and antiviral compounds and compositions and to new uses of these compositions in therapy. This specification also describes methods of use for the new compounds and compositions. The specification further describes methods for preparing these compounds. FIG. 1: A dual chamber apparatus for the preparation of NNDCT on site.

26 Claims, 1 Drawing Sheet

OTHER PUBLICATIONS

Prof. R. Noyori Nobel Lecture "Asymmetric Catalysis: Science and Opportunities" dated Dec. 8, 2001 (www.nobel.se/chemistry/ laureates/2001/noyori-lecture.pdf).
R. P. Singh and K. M. Shreeve, *Chem. Commun.*, 2001, pp. 1196-1197.
Ray Williams, "Periodontal Disease", New England Journal of Medicine 322: pp. 373-382, 1990.
Remington's Pharmaceutical Sciences, 17th ed., Mack Publishing Company, Easton, Pa., 1985, p. 1418.
Ryglowski, A et al, "The Facile Synthesis of Dialkyl 1-Aminoalkylphosphonates *Synth. Commun.*", pp. 2725-2731 (1994).
S. Kjelleberg, et al., "*Is there a role for quorum signals in bacterial biofilms?*" (PubMed—indexed for Medline).
Santaballa, J.A. et al., "Aqueous Chemistry of N-halo-compounds", *Chemical Society Reviews*, vol. 27, p. 453-460, 1998.
Scudiero DA, Shoemaker Rah, Paul KD, Monks A, Tierney S, Nofziger TH, Currens MJ, Seniff D, Boyd MR. Cancer Res.; Sep. 1;48 (17): pp. 4827-48733 1988.
Suzuki, A.*J. Organometallic Chem.*; 576, pp. 147-168 1999.
Suzuki, A. *Pure Appl. Chem.*; 66, p. 213-222 1994.
*Tetrahedron: Asymmetry*; 8 (13), pp. 2189-2192 1997.
The Chemical Formulary, H. Bennett Ed., Chemical Publishing Company, vol. XXXIV, pp. 163-171 1998.
Thomas EL.; Grisham MB, Jefferson MM. *Meth. Enzymol*; 132, pp. 585-593 1986.
V. V. Rozhkov, K. N. Makarov, R. G. Kostyanovsky, "N-Fluorination of aziridinecarboxylates via fluorolysis of their N-aminomethyl derivatives", *Mendeleev Commun.*, 1998, 66-67.
Webb, K. S. and Levy D. *Tetrahedron Lett.*; 36, p. 5117 1995.
Weiss S.J., Klein R., Slivka A., Wei M. *J. Clin. Invest.*; Sep.; 70(3): pp. 598-607 1982.
Yang, W.; Gao, S.; Wang, B. "Boronic Acid Compounds as Potential Pharmaceutical Agents"*Med. Res. Rev.*; 23, pp. 346-368 2003.
Yuan, C. et al, New Strategy for the Synthesis of Functionalized Phosphonic Acids, Heteroatom Chem.; 8 (2) pp. 103-122 1997.
Yuan, C., et al., New strategy for the Synthesis of Functionalized Phosphonic Acids, Pure Appl. Chem.; 68(4), pp. 907-912 1996.
Zboinska et al., *FEMS* Microbiol. *Lett.* 108, pp. 225-230 1993.
Zboinska et al., FEMS Microbiol. Lett., 70, pp. 23-28 1990.

Abrantes, et al.; "Determination of Extractable Biocides in Paper Food Packaging Materials Using Micellar Electrokinetic Chromatography"; J. Microcolumn Separations (1998), 10(5):387-391.
Kaminski, et al.; "N-Halo Derivatives IV: Synthesis of Low Chlorine Potential Soft N-Chloramine Systems"; Journal of Pharmaceutical Sciences (1976), 65(12):1733-1737.
Kaminski, et al.; "N-Halo Derivatives V: Comparative Antimicrobial Activity of Soft N-Chloramine Systems"; Journal of Pharmaceutical Sciences (1976), 65(12):1737-1742.
Kosugi, et al.; "N-Halo Derivatives VI: Microbiological and Chemical Evaluations of 3-Chloro-2-oxazolidinones"; Journal of Pharmaceutical Sciences (1976), 65(12):1743-1746.
Nagl, et al.; "Activity of N-chlorotaurine against herpes simplex and adenoviruses"; Antiviral Research (1998), 38:25-30.
Nagl, et al.; "Rapid Killing of *Mycobacterium terrae* by N-Chlorotaurine in the Presence of Ammonium is Caused by the Reaction Product Monochloroamine"; J. Pharm. Pharmacol. (1998), 50:1317-1320.
Nagl, et al.; "Tolerance of N-Chlorotaurine, a new Antimicrobial Agent, in infectious Conjunctivitis—A Phase II Pilot Study"; Ophthalmologia (2000), 214:111-114.
Nagl, et al.; "Enhanced Fungicidal Activity of N-Chlorotaurine in Nasal Secretion"; J. Antimicrobial Chemotherapy (2001), 47:871-874.
Nagl, et al.; "Impact of N-Chlorotaurine on Viability and Production of Secreted Aspartyl Proteinases of *Candida spp.*"; Antimicrobial Agents and Chemotherapy (2002), 46(6):1996-1999.
Roberts, et al.; "Chemistry of N-Halo Compounds. 33. Pyrolytic Eliminations from N,N-Dichloro Derivatives of Primary, Secondary, and Tertiary Alkyl Primary Amines"; J. Org. Chem. (1981), 46(21):4111-15.
Schmitz, et al.; "Conversion of 4-aminoheptane to pyrrolizidine"; Chemische Berichte (1960), 93:754-756.
White, et al.; "Relative Migratory Aptitudes in the Rearrangement of N,N-Dichlorocarbinamines by Aluminum Chloride"; J. Org. Chem. (1973), 38(22):3902-3908.
Zawalski, et al.; "A Convenient Preparation of N,N-Dibromoamines"; Synthetic Communications (1978), 8(8):549-562.
Zimmer, et al.; "Tert-butyl Hypochlorite as an N-Chlorinating Agent"; J. Am. Chem. Soc. (1954), 76:3856-3857.

\* cited by examiner

N-HALOGENATED AMINO ACIDS, N,N-DIHALOGENATED AMINO ACIDS AND DERIVATIVES; COMPOSITIONS AND METHODS OF USING THEM

This application claims the benefit of U.S. Provisional Application No. 60/647,366, filed Jan. 25, 2005, entitled "N-Halogenated Amino Acids, N,N-Dihalogenated Amino Acids and Derivatives; Compositions and Methods of Using Them" the disclosure of which is incorporated herein in its entirety.

FIELD OF THE INVENTION

The present invention relates to bactericidal, antibacterial, anti-infective, antimicrobial, sporicidal, disinfectant, antifungal, germicidal and antiviral compounds and compositions on the basis of amino acids and their derivatives that have the ability to release halogen and to new uses of these compositions in therapy. In another variation, the present invention relates to active bactericidal, antibacterial, anti-infective, antimicrobial, sporicidal, germicidal disinfectant, antifungal and antiviral compounds and compositions and to new uses of these compositions in killing microbes and therapy. Because of their valuable properties the new products and compositions of the invention also have broad applications in animal health including animal husbandry and agriculture, for example stock preservation of valuable seeds.

This specification also describes methods of use for the new compounds and compositions. The specification further describes methods for preparing these compounds. More specifically, these halogenated amino acids and their derivatives are also referred to herein as amino acids. Examples of natural amino acids are taurine, homotaurine, alanine, β-alanine, ornithine and γ-glutamic acid, or γ-aminobutyric acid (GABA). Non-exclusive examples of non-natural amino acids starting materials for the preparation of the halogenated amino acids include 1-amino-1-methylethanesulfonic acid, 2-amino-2-methylpropanesulfonic acid 1,1-dimethyl-2-amino-2-carboxy-ethanesulfonic acid, aminotrimethylene phosphonic acid, 2-amino-5-phosphonopentanoic acid, aminoethylphosphonic acid diesters, such as the diethylester, 1-amino-1-methylethane phosphonic acid, 1-amino-2-methylethane phosphonic acid, 1-amino-2-methylpropane phosphonic acid, leucine phosphonic acid, 4-amino-4-phosphonobutyric acid, (±) 2-amino-5-phosphonovaleric acid, (+)2-amino-5-phosphonovaleric acid, d,1-2-amino-3-phosphonopropionic acid, 2-amino-8-phosphonooctanoic acid, alanine boronic acid, β-alanine boronic acid or leucine boronic acid and their salts.

These starting materials may be used in form of their esters or salts. The lower alkyl esters of the phosphonic acids are the preferred esters for the preparation of the dihalo aminophosphonic acids of the invention and their derivatives. The term halogen as used herein includes fluoro, chloro, bromo and iodo.

The starting materials for the N-halo- or N,N-dihalo amino acids are generally known compounds or may be prepared by known methods. These materials are described in *Tetrahedron: Asymmetry* 1997, 8 (13), *FEMS Microbiol. Lett.*, 70, 23-28 (1990), Synth. Commun. 2725-2731 (1994), *FEMS Microbiol. Lett.* 108, 225-230 (1993), *Neurosci. Lett.* 21: 77-92 (1981), Br. *J. Pharmacol.* 75, 65, and for example, in Prof. R. Noyori Nobel Lecture "Asymmetric Catalysis: Science and Opportunities" dated Dec. 8, 2001

A number of the N-halogentated and N,N-dihalogenated amino acids are known. With respect to these amino acids, we provide new compositions with bactericidal, antibacterial, anti-infective, antimicrobial, antifuingal and antiviral properties.

The invention also relates to a number of new N,N-dihalogenated amino acids and their derivates with bactericidal, antibacterial, germicidal, anti-infective, sporicidal, antimicrobial, antifungal, and antiviral properties.

BACKGROUND OF THE INVENTION

A body's immune cells, the neutrophils and macrophages that are known for their abilities to clear infection can generate reactive oxygen metabolites that destroy and abnormal or neoplastic (cancerous) cells and modulate inflammatory responses. Neutrophils can be activated as a response to inflammatory stimuli, bacterial infection and/or other membrane changes. As a result, they produce super oxide radicals such as: HOO., $O_2$., and OH.. Under acidic conditions chloride ion ($Cl^-$) at physiological concentrations of 100-150 mM is oxidized by $H_2O_2$, which is catalyzed by myeloperoxidase (an enzyme within the neutrophils) to form hypochlorous acid (HOCl) following the reaction equation (Weiss S. J., Klein R., Slivka A., Wei M. *J Clin. Invest.* 1982, September; 70(3): 598-607):

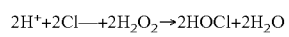

$$2H^+ + 2Cl^- + 2H_2O_2 \rightarrow 2HOCl + 2H_2O$$

Physiological generation of HOCl is tightly regulated through feedback inhibition by an intricate network of biochemical signals. HOCl is generated at a concentration of $2\times10^{-7}$ M per $10^6$ activated neutrophils (Lapenna D., Cuccurullo F. *Gen. Pharmacol.* 1996 October; 27(7): 1145-7). This quantity of HOCl is estimated to kill approximately $150\times10^6$ *E. coli* bacteria. Once HOCl is produced, it degrades rapidly by reacting with multiple oxidizable substrates within the complex cell system. Thus, the concentrations of reactive oxygen-metabolites are expected to fall to undetectable levels within hours. However, it has been demonstrated that neutrophils can use their HOCl to generate large quantities of a rather long-lived oxidants, such as N-chloramines. These long-lived oxidants are generated as monochloramines of taurine (NCT, or N-chlorotaurine) and dichloramines of taurine (NNDCT, or N,N-dichlorotaurine) depending on the pH of the environment. These oxidants are powerful antimicrobials and play key roles within the defense system as well as modulating the cytokines and growth factors in the host body.

DESCRIPTION OF RELATED ART

German Patent Application 4041703 W. Gottardi describes alkali metal salts of N-chlorotaurine. The application mentions that it has not been possible to isolate N-chlorotaurine as a pure substance but only in the form of a diluted solution when it is prepared in situ. Later work established that N-chlorotaurine could be prepared as described below. The German patent application also describes the preparation of pure alkali metal salts of N-chlorotaurine in crystalline form. It also discloses the use of these salts as disinfectants and bactericides in medicinal applications to humans. The German application describes the preparations of the alkali metal salts by the reaction of taurine with an alkali metal chloramide, such as N-chlorobenzene sulfonamide sodium (Chloramine-B) or N-chloro-4-methyl-benzene sulfonamide sodium (Chloramine-T). Chloramine-B and Chloramine-T are listed in the Merck Index, Thirteenth Edition, 2001, Entries 2084 and 2085 on page 356.

WO0222118 W. Gottardi et al. describe N-chlorotaurine, in particular in the form of its sodium salt as useful for the treatment of fungal infections, such as acute or chronic Rhinosinusitis or other fungal infections such as Otitis, Dermatitis, Bronchititis, diverse forms of pneumonia, such as *Pneumocystis carinii*, the fungal infections of sex organs, such as Colpitis, Endometritis, Balnitis, fungal infections of the gastrointestinal tract, such as Stomatitis, Oesophagitis, Enteritis, or fungal infections of the urethra, such as Pyelonephrititis, Ureteritis, Cystitis, or Urethritis.

Recently van Gelder et al. have synthesized and isolated N,N-dichlorotaurine as a powder (Gelder, N. M.; Bowers, R. Synthesis and characterization of N,N-dichlorinated amino acids: Taurine, Homotaurine, GABA and L-Leucine *J. Neurochemical Research.* 2001; 26:575-578). Their patent (U.S. Pat. 6,451,761 B1 Sep. 17, 2002, van Gelder and Bowers, "N'N'-dichlorinated omega-amino acids and uses thereof") describes the field as modifying amino acids to cross the blood brain barrier to reach the CNS. N-chlorotaurine (NCT) and N,N-dichlorotaurine (NNDCT) can be identified by their UV spectra. NNDCT has a maximum absorbance at 302 nm with a molar absorptivity of 332.9 $M^{-1}cm^{-1}$. These values are from Gottardi, W.; Nagl, M. *Arch. Pharm. Med. Chem.* 2002, 9, 411-421. NCT has a maximum absorbance at 252 nm with a molar absorptivity of 415 $M^{-1}cm^{-1}$.

Juan M. Antelo et al., *J. Chem. Soc., Perkin Trans.* 2, 2000, 2109-2114 described the general acid-base catalysis in the reversible disproportionation reaction of N-chlorotaurine. The authors also describe the preparation of solutions of N,N-dichlorotaurine by disproportionation of N-chlorotaurine at pH 2-2.5 and the stability of N,N-dichlorotaurine at pH=1.88. The loss of N,N-dichlorotaurine was less than 5% after 100 hours.

U.S. Patent Publication 2004/0022871 to Mainnemare published Feb. 5, 2004 describes pharmaceutical compositions including (i) at least a halogenated compound and (ii) at least a N-halogenated derivative of at least of a compound selected from zwitterionic compounds and/or amino acids. The halogenated compound is an alkaline metal hypochlorite, preferably sodium hypochlorite and the N-halogenated compound is an N-halogenated derivative of taurine. Amino acids included according to the U.S. Publication can be natural amino acids, derivatives and analogs of the latter. The disclosure of U.S. Patent Publication 2004/0022871 is incorporated herein by reference. The pharmaceutical compositions of this U.S. patent publication have been described as having anti-inflammatory, immuno-modulatory effect and tissue healing stimulation without exhibiting substantial stimulation of myeloperoxidase activity in a mammal. The hypochlorite titer of these pharmaceutical compositions is below or equal to 1 mole/liter of available chlorine, particularly of a hypochlorite of an alkaline metal, especially sodium hypochlorite. Its minimum titer is greater than or equal to about 1 picomole/liter. The N-chloramine titer of these compositions is less than or equal to about 5 moles/liter with a minimum of 0.01 femtomoles/liter.

SUMMARY OF THE INVENTION

It is understood that any aspect or feature of the present invention whether characterized as preferred or not characterized as preferred may be combined with any other aspect or feature of the invention, whether such other feature is characterized as preferred or not characterized as preferred. For example, a feature described as preferred, for example a pH range, or a specific pH for a particular composition (for example, certain N-halo- or N,N-dihalo amino acids of a specific formula) may be combined with another composition (N-halo- or N,N-dihalo amino acids of another specific formula) without deviating from the present invention. This statement also applies to any combination of substituents. For example, a substituent characterized as preferred may be combined with any other substituent not characterized as preferred. The terms "include(s)" or "comprise(s)" are used as open terms interchangeably in the text of this specification. Accordingly, in its broadest aspects the present invention provides pharmaceutical compositions which comprise or include an N-halo- or N,N-dihaloamino acid of the formula (I)

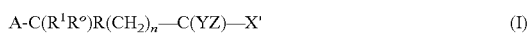

$$A\text{-}C(R^1R^o)R(CH_2)_n\text{---}C(YZ)\text{---}X' \tag{I}$$

or a derivative thereof. A is hydrogen, HalNH— or $Hal_2N$— wherein Hal is halogen selected from the group consisting of fluoro, chloro, bromo and iodo; R is a carbon carbon single bond or a divalent cycloalkylene radical with three to six carbon atoms, $R^1$ is hydrogen, lower alkyl or the group —COOH; $R^o$ is hydrogen or lower alkyl; n is 0 or an integer from 1 to 13, or $R^1$ and $R^o$ together with the carbon atom to which they attach form a $(C_3\text{-}C_6)$cycloalkyl ring; Y is hydrogen, lower alkyl or —$NH_2$ or —$NHal_2$; and Z is hydrogen or lower alkyl; and X' is hydrogen, —COOH, —$CONH_2$, —$SO_3H$, —$SO_2NH_2$, —$P(=O)(OH)_2$ or —$B(OH)_2$. If R is a divalent cycloalkylene radical n will not exceed the integer 11. That is, n may be 0, 1, 2, 3, 4, 5, 6, 7, 8, 9, 10, or 11. In other words the amino acid including the acidic group X' will have up to 16 chain atoms. In the divalent cycloalkylene radical or in the divalent radical —$(CH_2)_n$— one hydrogen may be substituted with —NHHal or —$NHal_2$. While the N-halo- or N,N-dihaloamino acids of the invention may contain up to 3 —NHHal or —$NHal_2$ groups, N,N-dihaloamino acids with 1 or 2 —NHHal or —$NHal_2$ groups are preferred. Most preferred are N,N-dihaloamino acids with 1 —$NHal_2$ group. This group may be in alpha-, beta-, gamma-, delta-, epsilon-, etc. to omega- position of the acidic groups $R^1$ (if $R^1$ is —COOH) or X'.

Derivatives of the compounds of formula I include pharmaceutically acceptable salts, esters with lower alkanols, lower alkanoyl derivatives of the —$NH_2$ group attached to the carbon atom to which the substituent X' is attached. The term "lower" in this respect includes residues with 1 to 6, preferably 1 to 4 carbon atoms.

In a preferred embodiment R is a carbon carbon single bond and n is 0 or an integer from 1 to 7, more preferably 0 or an integer from 1 to 5, and most preferably 0 or an integer from 1 to 3, that is 1, 2 or 3. Also of interest are the N,N-dihalo amino acids in which n=4 or n=5 or n=6 or n=7 or n=8 or n=9.

Compositions of the invention may often be utilized in liquid form, for example, as solutions, or suspensions, emulsions and the like. In that case the concentration of the N-halo- or N,N-dihaloamino acid or their derivatives will be up to 1 molar, or up to the saturation concentration of the N-halo- or N,N-dihaloamino acid or their derivatives. As used herein, the compositions further comprising a solvent may include water to form an aqueous composition, and the solvent may comprise aqueous and organic solvents and their combinations. A preferred composition of the invention comprises a composition having a concentration of the N-halo- or N,N-dihaloamino acid or its derivative between 0.1 to 100 mM and a pH range between about at pH 2.0, 3 to about 4.8, 3.0 to 4.5, or 3.5 to 4.5, or at about 3.5. The pH can be easily adjusted by various buffer systems known in the art. In one particular aspect of each of the above compositions, Hal is bromine, chlorine or iodine. In another aspect, Hal is bromine or chlorine.

Another composition has a concentration of the N-halo- or N,N-dihaloamino acid or its derivative between 0.01 mM to 1 M (molar) or about 0.1 to 50 mM and a pH range between about 2 to about 7, about 3 to about 6, 3 to about 4.8, about 3 to 4.5, or 3.5 to 4.5 or at about 3.5. Buffer systems may be used to adjust the pH to the desired value.

The present invention also provides new bactericidal, antibacterial, anti-infective, antimicrobial, germicidal, sporicidal, disinfectant, antiviral and antifungal compositions which include an N,N-dihalo-amino acid of the formula (II)

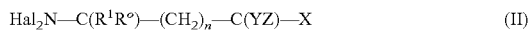

or a derivative thereof.

In the formula Hal is halogen selected from the group consisting of fluoro, chloro, bromo and iodo; $R^1$ is hydrogen, lower alkyl or the group —COOH; $R^o$ is hydrogen or lower alkyl, or $R^1$ and $R^o$ together with the carbon atom to which they attach form a ($C_3$-$C_6$)cycloalkyl ring; n is 0 or an integer from 1 to 3; Y is hydrogen, lower alkyl, —$NH_2$ or —$NHal_2$; and Z is hydrogen or lower alkyl; and X is —COOH, —$CONH_2$, —$SO_3H$ or —$SO_2NH_2$. In one particular aspect of each of the above compositions, Hal is bromine, chlorine or iodine. In another aspect, Hal is bromine or chlorine.

Derivatives of the compounds of formula II include pharmaceutically acceptable salts, esters with lower alkanols, lower alkanoyl derivatives of the —$NH_2$ group attached to the carbon atom to which the substituent X is attached. The term "lower" in this respect includes residues with 1 to 6, preferably 1 to 4 carbon atoms.

The pharmaceutically acceptable salts of compounds of formula (I), (II), (IIA), (III), (IIIA) or (IV) or their derivatives include salts with pharmaceutically acceptable cations. The compounds of formula (IIA), (III), (IIIA) and (IV) are described below. The salts of the N-halo- or N,N-dihaloamino acid includes salts of bases with the —COOH, —$CONH_2$, —$SO_3H$ or —$SO_2NH_2$ groups. Pharmaceutically acceptable salts also include ammonium, alkali metal, magnesium, or calcium salts and any organic amine salts. Alkali metal salts, Mg, Ca and Al salts are of interest. The alkali metal salts are of particular interest, particularly lithium, sodium, or potassium salts.

Examples of acid addition salts include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfates, toluenesulfonates, nitrates, phosphates, maleates, acetates, lactates and the like.

Lists of suitable salts are found in Remington's Pharmaceutical Sciences, 17th ed., Mack Publishing Company, Easton, Pa., 1985, p. 1418 or The Merck Index, Thirteenth Edition, 2001, Published by Merck Research Laboratories Division of Merck & Co., Inc. on pages MISC-22 and MISC-23, the disclosures of which are hereby incorporated by reference in their entirety.

The pharmaceutically acceptable acid addition salts of the —$NH_2$ group attached to the carbon atom to which substituent X is attached include salts among others with hydrochloric, sulfonic, phosphoric, nitric acid, benzenesulfonic, toluenesulfonic, methanesulfonic acid, camphorsulfonic acid and other acids.

Further derivatives of the compounds of formulae (I), (II), (IIA), (III), (IIIA) and (IV) include esters of the groups —COOH or —$SO_3H$ with lower alkanols and lower alkanoyl derivatives of the amino group attached to the carbon atom to which substituent X is attached.

Further derivatives of the compounds of formulae (I), (II), (IIa), (III), (IIIA) and (IV) also include the N-halo amino acids or the N,N-dihalo-amino acids in which certain groups of the amino acid molecule are protected by protecting groups. "Protecting group" means a chemical group that (a) preserves a reactive group from participating in an undesirable chemical reaction; and (b) can be easily removed after protection of the reactive group is no longer required.

"Amino-protecting group" means a protecting group that preserves a reactive amino group that otherwise would be modified by certain chemical reactions. Non-limiting examples of amino protecting groups include the formyl group or lower alkanoyl groups with 2 to 4 carbon atoms, in particular the acetyl or propionyl group, the trityl or substituted trityl groups, such as the monomethoxytrityl group, dimethoxytrityl groups such as the 4,4'-dimethoxytrityl or 4,4'-dimethoxytriphenylmethyl group, the trifluoroacetyl, and the N-(9-fluorenyl-methoxycarbonyl) or "FMOC" group, the allyloxycarbonyl group or other protecting groups derived from halocarbonates such as ($C_6$-$C_{12}$)aryl lower alkyl carbonates (such as the N-benzyloxycarbonyl group derived from benzylchlorocarbonate), such as the benzyloxycarbonyl (CBZ group), or derived from biphenylalkyl halo carbonates, or tertiary alkyl halo carbonates, such as tertiary-butylhalo-carbonates, in particular tertiary butylchloro-carbonate, or di(lower)alkyldicarbonates, in particular di(t-butyl)-dicarbonate, and the phthalyl group.

The invention described herein also includes N-monohalo amino acids of the formula

wherein Hal, $R^1$, $R^o$, n, Y, Z and X have the above-identified meanings; and their derivatives. Preferred are compounds of formula IIA, wherein $R^1$ is lower alkyl or the group —COOH; $R^o$ is lower alkyl, or $R^1$ and $R^o$ together with the carbon atom to which they attach form a ($C_3$-$C_6$)cycloalkyl ring; and their derivatives. In one particular aspect of each of the above compositions, Hal is bromine, chlorine or iodine. In another aspect, Hal is bromine or chlorine.

Derivatives of the compounds of formula IIA include pharmaceutically acceptable salts, esters with lower alkanols, lower alkanoyl derivatives of the —$NH_2$ group attached to the carbon atom to which the substituent X is attached. The term "lower" in this respect includes residues with 1 to 6, preferably 1 to 4 carbon atoms.

The pharmaceutically acceptable salts of compounds of formula (IIA) include salts with pharmaceutically acceptable cations. The salts of the N-halo amino acid include salts of bases with the —COOH and —$SO_3H$ groups. In one variation, the salts of the N-halo amino acid include salts of the compounds having the —$CONH_2$, —$SO_2NH_2$ groups. Pharmaceutically acceptable salts also include ammonium, alkali metal, magnesium, or calcium salts and any organic amine salts. Alkali metal salts, Mg, Ca and Al salts are of interest. The alkali metal salts are of particular interest, particularly lithium, sodium, or potassium salts.

Examples of acid addition salts include, but are not limited to, mineral or organic acid salts of basic residues such as amines; alkali or organic salts of acidic residues such as carboxylic acids, and the like. Pharmaceutically acceptable salts include, but are not limited to, hydrohalides, sulfates, methosulfates, methanesulfates, toluenesulfonates, nitrates, phosphates, maleates, acetates, lactates and the like.

Lists of suitable salts are found in Remington's Pharmaceutical Sciences, 17th ed., Mack Publishing Company, Easton, Pa., 1985, p. 1418 or The Merck Index, Thirteenth Edition, 2001, Published by Merck Research Laboratories Division of Merck & Co., Inc. on pages MISC-22 and MISC-23, the disclosures of which are hereby incorporated by reference in their entirety.

The pharmaceutically acceptable acid addition salts of the —$NH_2$ group attached to the carbon atom to which substituent X is attached include salts among others with hydrochloric, sulfonic, phosphoric, nitric acid, benzenesulfonic, toluenesulfonic, methanesulfonic acid, camphorsulfonic acid and other acids.

Further derivatives of the compounds of formula (IIA) include esters of the groups —COOH or —$SO_3H$ with lower alkanols and lower alkanoyl derivatives of the amino group attached to the carbon atom to which substituent X is attached.

Further derivatives of the compounds of formulae (IIA) also include N-halo-amino acids in which certain groups of the amino acid molecule are protected by protecting groups. "Protecting group" means a chemical group that (a) preserves a reactive group from participating in an undesirable chemical reaction; and (b) can be easily removed after protection of the reactive group is no longer required. Suitable protecting groups have been described earlier herein. N-halo-amino acids such as the N-fluoro-amino acid may be prepared using various methods known in the art for the fluorination of protected or unprotected amines and their derivatives. Similarly, the N,N-difluoro-amino acid may also be prepared using methods known in the art. See for example, R. P. Singh and K. M. Shreeve, *Chem. Commun.*, 2001, 1196-1197 (2001), and V. V. Rozhkov, K. N. Makarov, R. G. Kostyanovsky, "N-Fluorination of aziridinecarboxylates via fluorolysis of their N-aminomethyl derivatives", *Mendeleev Commun.*, 1998, 66-67 and references cited therein.

The term "composition" as used herein, refers to various forms of the compounds or compositions of the present invention, including solids such as powders, mixtures of powders and the like, emulsions, suspensions as well as solutions.

In one aspect, the compositions and their uses include known N,N-dihalo-amino acids or N-halo amino acids or their derivatives. In another aspect the compositions and their uses include new N,N-dihaloamino or N-halo amino acids or their derivatives. In either instance it is preferred that the compositions may be maintained in acidic form, that is at a pH below 7, for example 6.8, that is at a pH between about 2 to about 7, that is at a pH range between 2.0 to 6.8, 2.5 to 6.5, 2.5 to 6.0, or 2.5 to 5.0, or 3.0 to 5.0, or at a pH of about 3.5. Under different circumstances the pH may be kept below 5, that is, at a pH range of about 3 to 4.5, or 3.5 to 4.5, or at a pH about 3.5. While preferred are compositions where the pH of the composition is acidic, the selection of the pH will depend on many factors, including the specific use of the N,N-dihaloamino or N-halo amino acid (whether in vitro or in vivo), the type of the infection treated (for example, whether the infection is caused by bacteria, yeast, fungi or viruses), the site of the infection (for example, whether it is an infection of the eye, the larynx or the urethra or any target tissue or organ), the severity of the infection, the sensitivity of the patient, etc. As noted above, the desired pH can be easily achieved by the appropriate selection of buffer systems as well known to the person skilled in the art.

In some instances for the compositions of the invention, a pH between 7 and 9 may be suitable. In certain variations, the compositions may be maintained in a neutral, slightly basic or basic form; that is at a pH of about 7, for example 7.2, or for example at a pH between about 7 to about 9, that is at a pH range between 7.0 to 7.2, at a pH of about 7.2 to 7.5, at a pH of about 7.5 to about 8, or at a pH of about 8 to about 8.5, or at a pH of about 8.5 to about 9, or at a pH of about 8. Again, the required pH can be achieved by the use of suitable buffer systems known to a person skilled in the art. The desired pH may depend, in part, on the stability of the compounds and compositions as well as their intended applications.

In another aspect the composition, the solutions of the invention contain N,N-dihaloamino or N-halo amino acids in the concentration range of about 0.01 mM to about 1 M, or about 0.1 to 100 millimolar (mM).

In a further aspect the composition will be isotonic and physiologically balanced.

The N,N-dihaloamino and N-halo amino acids differ significantly from HOCl because they maintain an oxidizing potential with significant bactericidal activities, and yet they are less toxic than HOCl. N,N-dihaloamino or N-halo amino acids are also stable enough to diffuse some distance before oxidizing susceptible target molecules. The low molecular weight N,N-dihaloamino or N-halo amino acids of the present invention with n=0 or an integer up to 5 are more hydrophilic molecules.

Surprisingly, it has been found that, while the N,N-dihaloamino or N-halo amino acids of the invention have strong bactericidal, antibacterial, anti-infective, antimicrobial, sporicidal, disinfectant, antifungal and antiviral, they have low cytotoxicity. That is especially true when the compositions are acidic.

In a further aspect the compositions of the invention are stabilized to meet the requirement of being useable as compositions for the treatment or prevention of bacterial, microbial, germ, spore, fungal and viral infections or contaminations.

In another aspect the stabilization of the composition is provided by storing the compositions in a receptacle that will ensure sufficient stability to control bacterial, microbial, spore, fungal and viral infections or contaminations. In one aspect, the compositions as disclosed herein may be prepared to be sufficiently stable, or the composition having long term stability and shelf life for the intended applications for at least two weeks, preferably at least one month, preferably at least three months, more preferably at least six months, more preferably at least 12 months, and most preferably, at least about 24 months. Depending on the intended application for the compositions disclosed herein, the composition may be stored at room temperature or about 25° C., or below room temeprature, such as at about 20° C., 15° C. or at about 10° C.

The present invention provides pharmaceutical compositions which include an N,N-dihaloamino acid of the formula (III)

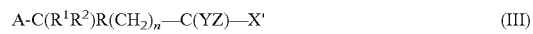

$$A-C(R^1R^2)R(CH_2)_n-C(YZ)-X' \qquad (III)$$

or a derivative thereof. A is hydrogen or $Hal_2N$— wherein Hal is halogen selected from the group consisting of fluoro, chloro, bromo and iodo; R is a carbon carbon single bond or a divalent ($C_3$-$C_6$)cycloalkylene radical with three to six carbon atoms, $R^1$ is hydrogen, lower alkyl or the group —COOH; $R^2$ is lower alkyl or $R^1$ and $R^2$ together with the carbon atom to which they attach form a ($C_3$-$C_6$)cycloalkyl ring; n is 0 or an integer from 1 to 13; Y is hydrogen, lower alkyl or —$NH_2$ or —$NHal_2$; and Z is hydrogen or lower alkyl; and X' is hydrogen, —COOH, —$CONH_2$, —$SO_3H$, —$SO_2NH_2$, —P(=O)(OH)$_2$ or —B(OH)$_2$. If R is a divalent ($C_3$-$C_6$)cycloalkylene radical n will not exceed the integer 11. In other words the amino acid including the acidic group X' will have up to 16 chain atoms. Optionally, in the divalent ($C_3$-$C_6$)cycloalkylene radical or the divalent radical —$(CH_2)_n$—, one hydrogen may be substituted with —32NHal$_2$. While the N,N-dihaloamino acids of the invention may contain up to 3 —NHal$_2$ groups, N,N-dihaloamino acids with 1 or 2-NHal$_2$ groups are preferred. Most preferred are N,N-dihaloamino acids with 1 —NHal$_2$ group. This group may be in alpha-, beta-, gamma-, delta-, epsilon-, etc. to omega- position of the acidic groups R$^1$ (if R$^1$ is —COOH) or X'. Also included are N-monohalo amino, in particular N-monochloro amino, acids and their derivatives wherein the —NHal$_2$ group of formula III is replaced with an —NHHal group [formula (IIIA)].

Derivatives of the compounds of formula III or IV (described below) include pharmaceutically acceptable salts, esters with lower alkanols, lower alkanoyl derivatives of the —NH$_2$ group attached to the carbon atom to which the substituent X or X' is attached, and their N-monohalo amino acid derivatives. The term "lower" in this respect includes residues with 1 to 6, preferably 1 to 4 carbon atoms.

In a preferred embodiment R is a carbon carbon single bond and n is 0 or an integer from 1 to 7, more preferably 0 or an integer from 1 to 5, and most preferably 0 or an integer from 1 to 3.

In another aspect a composition with bactericidal, antibacterial, anti-infective, antimicrobial, sporicidal, disinfectant, antifungal and antiviral activity is provided comprising an N,N-dihaloamino acid of the formula (IV)

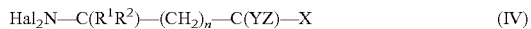

Hal$_2$N—C(R$^1$R$^2$)—(CH$_2$)$_n$—C(YZ)—X  (IV)

or a derivative including N-monohalo derivative thereof; wherein Hal is halogen selected from the group consisting of fluoro, chloro, bromo and iodo; R$^1$ is hydrogen, lower alkyl or the group —COOH; R$^2$ is lower alkyl or R$^1$ and R$^2$ together with the carbon atom to which they attach form a (C$_3$-C$_6$)cycloalkyl ring; n is 0 or an integer from 1 to 3; Y is hydrogen, lower alkyl or —NH$_2$; and Z is hydrogen or lower alkyl; and X is —COOH, —CONH$_2$, —SO$_3$H or —SO$_2$NH$_2$; the derivative being selected from the group consisting of pharmaceutically acceptable salts, esters with lower alkanols, and lower alkanoyl derivatives of the —NH$_2$ group attached to the carbon atom to which the substituent X is attached.

In another aspect, the above-described composition comprising a new N,N-dihaloamino acid of the formula (W) is one in which R$^1$ is hydrogen, or lower alkyl; n is 0, 1 or 2; Y is hydrogen or lower alkyl; Z is hydrogen or lower alkyl; and X is —SO$_3$H or —SO$_2$NH$_2$; or a derivative thereof; the derivative being selected from the group consisting of pharmaceutically acceptable salts or esters with lower alkanols.

In a further aspect, the above-described compositions comprising a new N,N-dihaloamino acid of the formula (IV) are ones in which wherein Y and Z are hydrogen; X is —SO$_3$H; the derivative being selected from the group consisting of pharmaceutically acceptable salts. In another aspect, Hal is chloro.

The preferred derivatives are pharmaceutically acceptable salts.

In another aspect, the above-described compositions include the following compounds or a derivative thereof; the derivative being selected from the group consisting of pharmaceutically acceptable salts and esters with lower alkanols:

N,N-dichloro-2,2-dimethyltaurine;
N-chloro-2,2-dimethyltaurine;
N,N-dichloro-1,1,2,2-tetramethyltaurine;
N-chloro-1,1,2,2-tetramethyltaurine;
N,N-dibromo-2,2-dimethyltaurine;
N-bromo-2,2-dimethyltaurine;
N,N-dibromo-1,1,2,2-tetramethyltaurine;
N-bromo-1,1,2,2-tetramethyltaurine;
N,N-diiodotaurine;
N-iodotaurine;
N,N-dichloro-2-methyltaurine;
N-chloro-2-methyltaurine;
N,N-dichloro-2,2,3,3-tetramethyl-β-alanine;
N-chloro-2,2,3,3-tetramethyl-β-alanine;
N,N-dichloro-3,3-dimethylhomotaurine;
N-chloro-3,3-dimethylhomotaurine;
N,N-dichloro-2-methyl-2-amino-ethanesulfonic acid;
N-chloro-2-methyl-2-amino-ethanesulfonic acid;
N,N-dichloro-1-methyl-2-amino-ethanesulfonic acid;
N-chloroaminotrimethylene phosphonic acid;
N,N-dibromo-2-amino-5-phosphonopentanoic acid;
N-bromo-2-amino-5-phosphonopentanoic acid;
N,N-dichloro aminoethylphosphonic acid diesters, such as the diethylester;
N-chloro aminoethylphosphonic acid diesters, such as the diethylester;
N,N-dichloro-1-amino-1-methylethane phosphonic acid;
N-chloro-1-amino-1-methylethane phosphonic acid;
N,N-dichloro-1-amino-2-methylethane phosphonic acid;
N-chloro-1-amino-2-methylethane phosphonic acid;
N,N-dichloro-1-amino-2-methylpropane phosphonic acid;
N-chloro-1-amino-2-methylpropane phosphonic acid;
N,N-dichloro leucine phosphonic acid;
N-chloro leucine phosphonic acid;
N,N-dichloro-4-amino-4-phosphonobutyric acid;
N-chloro-4-amino-4-phosphonobutyric acid;
(±) N,N-dichloro-2-amino-5-phosphonovaleric acid;
(±) N-chloro-2-amino-5-phosphonovaleric acid;
N,N-dichloro (+)2-amino-5-phosphonovaleric acid;
N-chloro (+)2-amino-5-phosphonovaleric acid;
N,N-dichloro d,1-2-amino-3-phosphonopropionic acid;
N -chloro d,1-2-amino-3-phosphonopropionic acid;
N,N-dichloro-2-amino-8-phosphonooctanoic acid;
N-chloro-2-amino-8-phosphonooctanoic acid;
N,N-dichloro leucine boronic acid;
N-chloro leucine boronic acid;
N,N-dichloro-β-alanine boronic acid; or
N-chloro-β-alanine boronic acid;

or a pharmaceutically acceptable salt or ester thereof.

In another aspect, the compositions described herein comprising a mono-or dihaloamino acid of the formula (I), (II), (IIA), (III), (IIIA) or (IV) or their derivatives are ones in which Hal is chloro. In yet another aspect, the compositions described herein comprising a mono-or dihaloamino acid of the formula (I), (II), (IIA), (III), (IIIA) or (IV) or their derivatives are ones in which Hal is bromo or chloro.

In another aspect, the compositions of the invention further comprises a pharmaceutically acceptable carrier.

The phosphonic or boronic acids of the invention may be combined with a dihydroxy compound with up to ten carbon atoms which may be acyclic or cyclic having at least two hydroxyl groups attached to two different carbon atoms, such as ethylene glycol, 2-amino-2-(hydroxymethyl)-1,3-propane diol, mannitol, diethylene glycol, 1,2-hexane diol, glycerol, diethanolamine, pinacol or other similar dihydroxy compounds. In some cases this combination enhances the stability of the boronic or phosphonic acids of the invention.

Again, all the features, characteristics and ranges described for the invention, in any aspect, whether described as of interest or as particular or not, may be combined with each other. For example, a substituent of interest in the formulae depicted herein may be combined with another more broadly defined, not emphasized substituent described herein. For example, the substituent X being —SO$_3$H may be combined with substituents Y or Z other than hydrogen.

The invention also includes pharmaceutical compositions wherein the halo amino acids of formulae (I), (II), (IIA), (III), (IIIA) or (IV) or their derivatives are combined with halogenated compounds derived from hypohalous acid derivatives or a source of a hypohalous acid derivative. Such hypohalous derivatives includes a hypohalous acid or a source of hypohalous acid or a salt of a hypohalous acid, in particular sodium or potassium hypochlorite. Such pharmaceutical compositions have anti-inflammatory, immuno-modulatory, bactericidal, antibacterial, anti-infective, antimicrobial, sporicidal, disinfectant, antifungal and antiviral effect and tissue healing stimulation without exhibiting substantial stimulation of myeloperoxidase activity in a mammal. The hypochlorite titer of these pharmaceutical compositions is below or equal to 1 mole/liter of available chlorine, particularly of a hypochlorite of an alkaline metal, especially sodium hypochlorite. Its minimum titer is greater than or equal to about 1 picomole/liter. The N-chloramine titer of these compositions is less than or equal to about 5 moles/liter with a minimum of 0.01 femtomoles/liter. Again among the hypohalous derivatives, the chloro, bromo and iodo derivatives would be preferred. More preferred compounds are the chloro and bromo derivatives. Most preferred are the chloro derivatives.

Processes for the Preparation of N-Halo-amino Acids, N,N-Dihalo-amino Acids and their Derivatives The N-halo-amino acids and N,N-dihaloamino acids and derivatives are prepared by the reaction of the amino acid or a derivative thereof from which the halogenated amino acids are produced with a halogen source under reaction conditions which lead to the replacement of one or two hydrogen atoms at the -amino group of the amino acid with one or two halogen atoms, that is fluoro, chloro, bromo or iodo atoms. These processes are known to chemists skilled in the art.

In one aspect of the invention, the amino acids that are used as starting materials include taurine, homotaurine, β-alanine, ornithine and γ-glutamic acid, and γ-aminobutyric acid (GABA), 1-amino-1-methylethanesulfonic acid, 2-amino-2-methylpropanesulfonic acid, or 1,1-dimethyl-2-amino-2-carboxy-ethanesulfonic acid, and others. For example, aminotrimethylene phosphonic acid or its salts, 2-amino-5-phosphonopantanoic acid or its salts, aminated (1R,2S)-(1,2-epoxypropyl)phosphonic acid (or aminated fosfomycin), 2-aminoethylphosphonic acid diesters, such as the diethylester, 1-amino-1-methylethane phosphonic acid, 1-amino-2-methylethane phosphonic acid, 1-amino-2-methylpropane phosphonic acid, leucine phosphonic acid, 4-amino-4-phosphonobutyric acid, (±)2-amino-5-phosphonovaleric acid, (+)2-amino-5-phosphonovaleric acid, d,1-2-amino-3-phosphonopropionic acid or 2-amino-8-phosphonooctanoic acid may be used. In another aspect, these starting materials may be used in form of their esters or salts. In another aspect, the lower alkyl esters of the phosphonic acids are the preferred esters for the preparation of the halo phosphonic acids of the invention and their derivatives. All these starting materials are either well-known, commercially available, or may be prepared by well-known methods of preparation. A number of the starting materials are commercially available, for example from Sigma-Aldrich.

The following non-exclusive halogen sources may be used to produce the N-halo amino acids and their derivatives: HOCl or its salts (for example, NaOCl or KOCl), N-haloarylsulfonamide salts, wherein the aryl group contains from 6 to 15 carbon atoms with 1 or 2 aromatic rings, 6 to 10, or 6 to 8, carbon atoms and one aromatic ring, such as N-halobenzenesulfonamide or N-halo-4-alkylbenzenesulfonamide, wherein the alkyl group is lower alkyl from 1 to 4 carbons, methyl or ethyl. The N-halobenzene-sulfonamides or N-halo-4-alkylbenzenesulfonamides are often used in form of their salts, for example, alkali salts, for example, their sodium or potassium salts. The most frequently used reagents will be N-chlorobenzenesulfonamide and N-chloro-4-methyl-benzenesulfonamide in form of their sodium salts, because they are readily commercially available. Other non-limiting halogen releasing agents or sources may be HClO$_2$, N-chloro-succinimide or N-bromosuccinimide, N-iodosuccinamide, Cl$_2$, Br$_2$, I$_2$, thionylchloride, phosgene, PCl$_3$, PCl$_5$, and chlorinating agents, such as those used in swimming pools, or combinations of the agents.

Other amino acid starting materials include 2,2-dimethylhypotaurine, 1,1,2,2-tetramethyl-hypotaurine, 2,2-dimethyltaurine, 1,1,2,2-tetramethyltaurine, 2,2,3,3-tetramethyl-β-alanine, and 3,3-dimethylhomotaurine.

If one molecule of the halogen source releases one halogen, obviously for each starting amine of the amino acid or derivative molecule at least one or two molecules of the halogen source will be used to achieve the desired halogenation. More details of the preparation of N-halo amino acids and their derivatives are set forth in the examples.

When not commercially available the phosphonic acid starting materials for the preparation of the compounds of the present invention may be prepared according to procedures well known to one skilled in the art. See for example Yuan, C. et al, New Strategy for the Synthesis of Functionalized Phosphonic Acids, Heteroatom Chem. 1997, 8 (2) 102-122; Yuan, C., et al., New strategy for the Synthesis of Functionalized Phosphonic Acids, Pure Appl. Chem. 1996, 68(4), 907-12; A Versatile Route to Substituted Organophosphonic Acids, J. Am. Chem. Soc., 1990, 31, 2933; G. M. Kosolapoff, The Synthesis of Phosphonic and Phosphinic Acids, Organic Reactions, Vol. 6 (1951), and references cited therein.

The boronic acid starting materials and their esters are available commercially from, for example, Acros Organics (Fischer Scientific) or Ryscor Science, Inc. (Raleigh, N.C.), among other companies, or may be prepared according to procedures known to one skilled in the art. See for example, Webb, K. S. and Levy D. *Tetrahedron Lett.* 1995, 36, 5117; Suzuki, A. *Pure Appl. Chem.* 1994, 66, 213; Miyaura, N. and Suzuki, A. Chem. Rev. 1995, 95, 2457-2483; Suzuki, *A. J Organometallic Chem.* 1999, 576, 147-168; Kamatani, A. and Overman, L. E. *J. Org. Chem.* 1999, 64, 8743-8744, Yang, W.; Gao, S.; Wang, B. "Boronic Acid Compounds as Potential Pharmaceutical Agents" *Med. Res. Rev.* 2003, 23, 346-368, and references cited therein and Brown, H. C.; Midland, M. M.; Levy, A. B.; Kramer, G. W., "Organic Synthesis via Boranes" Wiley-Interscience: New York, 1975.

Compounds according to the present invention can also include their individual stereoisomers (enantiomers and diastereoisomers) as well as the racemic mixtures of the compound. The individual isomers, such as the pure R, S, RR, SS, RS, SR, etc. may be prepared by treating the isomeric mixture with an optically active resolving agent to form a pair of diastereoisomeric compounds. The diastereoisomeric compounds may be separated and the optically pure enantiomer or diastereomer may be isolated using procedures well known in the art. Because diastereomers have distinct physical properties (such as the melting points, boiling points, solubilities, reactivity, etc.), they can be readily separated by taking advantage of these dissimilarities. The diastereomers can be separated by chromatography or, preferably, by separation or resolution techniques based upon differences in solubility. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981) and references cited therein.

A typical reaction scheme to prepare the N,N-dihaloamino acids, as exemplified for the preparation of the N,N-dichloroamino acid, can be depicted as follows:

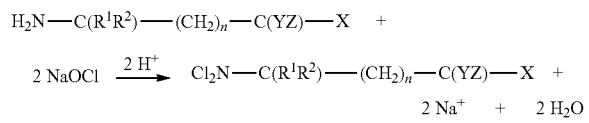

in which $R^1$, $R^2$, n, X, Y and Z have the above-described meanings.

Should the preparation of the various N-haloamino acids be required, the reaction described above may simply be modified by using 1 equivalent of NaOCl instead of two equivalents under neutral or alkaline conditions.

The amino acid starting material is dissolved in a lower alkanol (for example, methanol or ethanol) and made acidic. To this solution an aqueous NaOCl solution is added. The reaction results in the chlorination of the amino group and the precipitation of sodium chloride. The solvent is evaporated at low temperatures, for example, below 30° C. and a residue is obtained. The residue is taken up in a solvent and the N-haloor N,N-dihaloamino acid isolated by extraction with a solvent not miscible with the aqueous lower alkanol phase. Similarly the N-halo- or N,N-dihalo-amino acid may be prepared by reacting the amino acid starting material with HOCl.

Accordingly, the bromo analogs may also be prepared with NaOBr as the halogenating agent.

According to J Marcinkiewicz et al. 2000 (*J of Inflammatory Research* 49, 280-289) NNDCT (N,N-dichlorotaurine) may be synthesized in solution by reacting HOCl with taurine at pH 5. NNDCT also can be generated in the oxidation of Bunte salt ($H_2NCH_2CH_2S$—$SO_3H$) (Chinake et al. Oxyhalogen-sulfur chemistry: kinetics and mechanism of the oxidation of a Bunte salt 2-aminoethanethiolsulfuric acid by chlorite. *Phys. Chem. Chem. Phys.* 2001; 3:4957-4964) and hypotaurine ($H_2NCH_2CH_2SO_2H$) by chlorite ($ClO_2^-$) (Martincigh, B. S.; Mundoma, C.; Simoyi, R. H.; Antioxidant chemistry: Hypotaurine-taurine oxidation by chlorite. *J. Phys. Chem. A.* 1998; 102:9838-9846).

The reactions are shown in equations 1-6:

$$2 ClO_2^- + H_2NCH_2CH_2S\text{—}SO_3H \longrightarrow \quad (1)$$
$$\text{Bunte salt}$$
$$ClNHCH_2CH_2SO_3H + SO_4^{2-} + Cl^- + H^+$$
$$\text{N-chlorotaurine}$$

N-chlorotaurine disproportionates to form N,N-dichlorotaurine and taurine in acidic solution:

$$2 ClNHCH_2CH_2SO_3H \longrightarrow Cl_2NCH_2CH_2SO_3H + \quad (2)$$
$$\text{N,N-dichlorotaurine}$$
$$NH_2CH_2CH_2SO_3H$$
$$\text{Taurine}$$

$$ClO_2^- + H_2NCH_2CH_2SO_2H + H^+ \longrightarrow \quad (3)$$
$$\text{Hypotaurine}$$
$$H_2NCH_2CH_2SO_3H + HOCl$$
$$\text{Taurine}$$

HOCl can rapidly oxidize the remaining hypotaurine to taurine:

$$HOCl+H_2NCH_2CH_2SO_2H \rightarrow H_2NCH_2CH_2SO_3H+ \quad (4)$$
$$Cl^-+H^+$$

or oxidize hypotaurine to N-chlorohypotaurine:

$$HOCl+H_2NCH_2CH_2SO_2H \rightarrow ClHNCH_2CH_2SO_2H+ \quad (5)$$
$$H_2O$$

In highly acidic conditions, HOCl oxidizes N-chlorohypotaurine to N, N-dichlorotaurine.

$$HOCl+ClHNCH_2CH_2SO_2H \rightarrow Cl_2NCH_2CH_2SO_3H+ \quad (6)$$
$$H_2O+HCl$$

Under less acidic conditions the reaction can be stopped at the N-chlorohypotaurine level.

The compounds with at least one lower alkyl group attached to the carbon atom to which the amino group is attached are more stable mono- and dihalogenated amino acids.

These compounds may be prepared as follows:

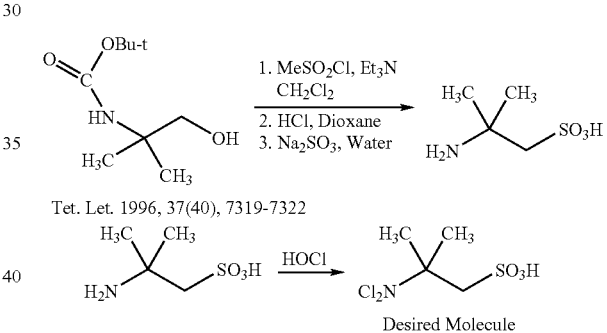

Tet. Let. 1996, 37(40), 7319-7322

Derivatives of the N,N-dihalo-amino acids may be prepared by protecting the amino group with an amino-group protecting agent as disclosed herein, for example, by forming the benzyloxycarbonyl (CBZ) derivative, followed by the formation of the sulfonyl chloride which may be converted into sulfonamides, for example with a lower alkyl amine, such as methylamine. Similarly, the sulfonyl chloride may be reacted with benzylamine, and the resulting benzylsulfonamide may be converted to the group —$SO_2NH_2$. Thereafter the protecting group may be removed by methods known per se to chemists skilled in the art. A comprehensive list of suitable protecting groups that may be used may be found in T. W. Greene, *Protecting Groups in Organic Synthesis*, 3rd edition, John Wiley & Sons, Inc. 1999.

A representative example of one method for the preparation of 2-amino-2-methylpropanesulfonic acid is shown in the reaction scheme below:

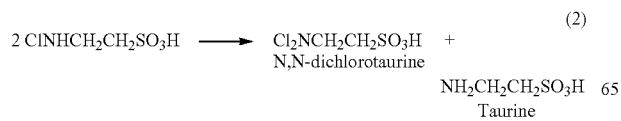

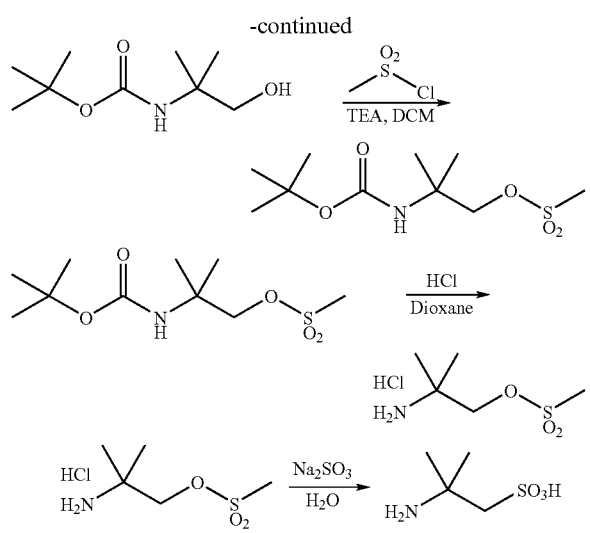

A representative procedure for the preparation of the compound 2-amino-2-methylpropanesulfonic acid is provided in the experimental section.

Pharmaceutically-acceptable salts of the compounds of the invention may be prepared by reacting the free acid or base forms of these compounds with a stoichiometric or greater amount of the appropriate base or acid in water or in an organic solvent, or in a mixture of the two; generally, for example, non-aqueous media like ether, ethyl acetate, ethanol, isopropanol. The salts of the invention may also be prepared by ion exchange, for example.

Salts may also be prepared by reacting the N-halo- and N,N-dihaloamino acids in other manners known per se including a method analogous to the method described in German Patent Application 4041703 W. Gottardi.

The sodium salts of the N-halo- or N,N-dihaloamino acids may be converted into the lower alkyl esters by reacting the sodium salt with a lower dialkyl sulfate, such as dimethyl or diethyl sulfate in the presence of sodium bicarbonate.

The amides in which the substituent X or X' is —CO$_2$—NH$_2$ are produced in a manner well-known to chemists skilled in the art.

Methods of Use for the N-halo- or N,N-dihaloamino Acids and Derivatives

The N-halo- or N,N-dihaloamino acids and their derivatives are antimicrobial agents which kill microbes at relatively low concentrations and can be tolerated by eukaryotic cells at significantly high concentrations. In the preferred N-halo- or N,N-dihaloamino acids, halo is chloro, bromo or iodo. This range of therapeutic activity and favorable therapeutic index is absolutely critical considering the physiological role of chloramines in the destruction of pathogens in vivo. For an antimicrobial product that is applied to vital, soft and sensitive tissues such as ophthalmic, skin or any other sensitive areas its safety and efficacy cannot be compromised. Thus, use of such product(s) in humans for treating infections is supported by our positive results.

The compounds of Formulae (I), (II), (IIA), (III), (IIIA) or (IV) have the following potential areas of application: contact lens cleanser, bacterial inactivation, ophthalmic, general surgical preparation including oncology, surgical instrument disinfection, medical device and instrument disinfection, dental instruments disinfection and application in food sanitation including disinfection of surface areas. They are also useful in vaccine formulations (as preservative and potentially adjuvant), as compounds with viricidal effect, for the viral inactivation of both DNA and RNA classes of viruses including HIV, hepatitis A, respiratory syncytial virus, Adenovirus, West Nile virus, HSV-1, HSV-2, SARS, influenza and para-influenza viruses, picornaviruses, and vaccinia virus (as a Model for Poxviruses). In addition, these compounds are also useful for the treatment of fungal infections, such as acute or chronic Rhinosinusitis or other fungal infections such as Otitis, Dermatitis, Bronchititis, Pneumonia's such as *Pneumocystis carinii*, the fungal infections of sex organs, such as Colpitis, Endometritis, Balnitis, fungal infections of the gastrointestinal tract, such as Stomatitis, Oesophagitis, Enteritis, or fungal infections of the urethra, such as Pyelonephrititis, Ureteritis, Cystitis, or Urethritis. Furthermore, the compositions described herein have antimicrobial activity against many other microorganisms, including *Escherichia coli, Listeria monocytogenes, Staphylococcus aureus*, methicillin-resistant *S. aureus* (MRSA), *Pseudomonas aeruginosa, Lactobacillus*, yeast, vancomycin-resistant enterococcus, molds, and spores, including spores of anthrax and cysts of Acanthamoeba. In particular, the solutions of the present invention may be useful in the treatment of several different strains of Bacillus anthracis. Vancomycin-resistant bacteria, MRSA, and others are easily destroyed by the compositions of the present invention. Examples of bacteria implicated in periodontal disease and destroyed by the compositions of this invention are *Bacteriodes gingivalis, B. intermedius, Actinomyces actinomycetemcomitans* and *B. forsythus*. Examples of bacteria that are implicated in mastitis (infection of cow udder) and killed by the compositions are *Streptococcus agalactiae* and *Streptococcus infantarius*. The compositions destroy biofilms and are therefore effective against microbes growing in both planktonic form and in biofilms.

In a further aspect of the invention, there is provided a method for the treatment of various medical conditions selected from the groups consisting of promoting wound healing, reduction of pathogens in open wounds, wound decontamination, wound bed irrigation/preparation, ocular disinfection or decontamination, oral disinfection, nasopharyngeal therapy, antiflugal therapy, ophthalmic, oral surgery and dentistry, otology applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis or other diseases that produces biofilms, treatment of viral infections, treatment of skin diseases, and tissue repair and regeneration, which method comprises using the solution of the invention by applying the solution to the site where treatment is required such as pre- and post operative surgery, cardiovascular, re-secting solid tumor in oncology.

As an example, the dosage for use on chronic wounds of an approximate size of 25 square cm might be in the range of 30 ml of solution containing 2 to 200 mg of active ingredient where the active ingredient is NNDCT, and the solution may be applied from one to ten times per day or as deemed necessary for effectively treating the wound. In certain instances the composition may contain 0.01 mM to 1 M, or about 0.1 to 100 mM of active ingredient. Dosages in other applications would be adjusted to the local area depending on where the antimicrobial activity is required and the severity of infection.

The Compositions of the Invention

In one aspect the compositions in form of solutions are osmotically balanced, and have minimal cytotoxicity. In another aspect, the compositions are not osmotically balanced and have minimal cytotoxicity.

In another aspect the compositions described herein have a therapeutic index of about 1000 to about 5,000, defined by the ratio of their 50% inhibitory concentration cytotoxicity index ($IC_{50}$) at one hour against both L929 mouse lung epithelial cells and primary human fibroblasts to their Minimum Bactericidal Concentration against Escherichia coli ATCC 11229 at 37° C. for one hour.

Because the compositions of the present invention are non-toxic and have antibacterial properties, they are useful in any application in which antimicrobial properties are desirable. Such applications include, without limitation, treatment of wounds, burns, and canker sores; irrigation; the treatment of various fungal infections such as onychomycosis (fungal nail infections on fingers and toes) cleaning of tissue sites (e.g., pre- and post-operative); ophthalmic applications (e.g., in contact lens cleaning solutions or for irrigation of the eye before, during, or post ophthalmic surgery); for dermatological applications, facial cleansing of microbial infection, cold sore, pimples, psoriasis; and numerous applications which are readily apparent to one skilled in the art, such as dental applications including the treatment of gingivitis or periodontitis, and animal health applications (including treatment of mastitis). Application also includes the elimination or reduction of pathogens on surfaces including medical equipment, instruments, organ preservation, implant disinfection, devices or food (without limiting to meat, fruits, vegetables) and food contact surfaces including the elimination or reduction bacterial biofilms. Unlike many anti-infective compositions used in similar applications, the compositions of the invention have minimal to no side effects.

The compositions of the invention which comprise N-halo- or N,N-dihaloamino acids of the formulae (I), (II), (IIA), (III), (IIIA) or (IV) and their derivatives may be incorporated into a variety of applications, including bandages or wound dressings. The compositions in form of physiologically balanced, acidic solutions may be used in combination with specially designed bandages in a wound treatment protocol. The specialized bandage may include an opening or "window" through which topical treatment materials such as the solution of the present invention may be applied. The compositions may also be applied in applications (for example treatment of burns) where it is desirable to maintain a moist and sterile environment without disturbing the dressing. In one such example a perforated tube is placed between the dressing and the outer bandage or wrap. Periodically the composition is passed through the tube thus irrigating the dressing with fresh antimicrobial solution.

Also disclosed herein is an article of manufacture comprising the composition of the invention packaged in a container. Surfaces of the container which are in contact with the composition of the invention are made of material which is not reactive with an oxidizing agent.

The stability of a solution of N-halo- and N,N-dihaloamino acids and their derivatives permits the use of different forms of packaging that would be practical for use by patients. The solution may be packaged in several single-use 20 to 40 ml or 30 ml clear or amber glass bottles with Teflon-lined screw caps and sealed with tape to ensure gas tightness. In one aspect, the same solution may be packaged in a 250 ml amber glass bottle or in a 250 ml non-reactive plastic bottle. However, up to 5 liter bottles may be used, because such larger volumes are practical for treatment of burns. Storage in these receptacles ensures long-term stability required for the uses of the compositions described herein in detail. For example, a solution of N,N-dichlorotaurine within the concentration range described herein in a vial stored in a refrigerator will have a loss of no more than 13% of N,N-dichlorotaurine at time t=0 after a period of three months. Additionally, packaging may include a dual chamber system where component A is mixed with component B to form the final product, N,N-dihaloamino acid or its derivatives. The N-halo- and N,N-dihaloamino acids may be used in appropriate concentrations and delivery vehicles or carriers that are non-irritating and suitable for delivering the active compound to the intended site of action, such as lotions, solutions, creams, emulsions, ointments, balms, pastes, sprays, aerosols, gels, patches, solids, sticks, aqueous solutions, organic solvents, or other foundation compositions. Generally, such carrier systems can be described as being solutions, creams, emulsions, gels, solids and aerosols. Delivery may also include special means for delivery, such as a pessary or suppository. The compounds may also be incorporated as active agents or inactive precursors into or onto medical devices, such as catheters, stents, pace makers, needles or tubings.

In one aspect, the solutions of the present invention may be stored in single-use containers. In another aspect, the solutions of the invention may be stored in single-use containers of various different sizes, configurations, and having different volumes as suitable for the desired applications as disclosed herein. In some applications, for example, the solution of the invention may be stored in single-use 30 mL, optionally disposable containers. In one aspect the present composition may be stored as powder together with pharmaceutically accepted excipients under inert gas at room temperature.

The compositions of the invention may include the following pharmaceutically acceptable carriers: sodium chloride to attain isotonicity, buffers, stabilizers, solvents, flavoring agents (in case of oral or nasopharyngeal administration and food industry), preserving agents, diluents, extenders and other auxiliary substances or excipients. Specific examples of pharmaceutically acceptable carriers and excipients that may be used are described in Remington: The Science and Practice of Pharmacy, A. Gennaro, ed., 20th edition, Lippincott, Williams & Wilkins, Philadelphia, Pa.; Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995), the disclosures of which are incorporated herein in their entirety. In general, water, a suitable oil, saline, lower alcohols, and glycols such as propylene glycol or polyethylene glycols may be suitable carriers for solutions. In one aspect solutions contain the active ingredient in a water soluble or aqueous medium soluble form, for example as a salt, together with suitable stabilizing agents, and if necessary, buffer substances. In addition, solutions may contain preservatives, such as benzalkonium chloride, methyl- or propyl-paraben, and chlorobutanol. Suitable pharmaceutical carriers are described in Remington: The Science and Practice of Pharmacy, the above-identified standard reference text in this field.

The compositions may further comprise other active ingredients, such as HOCl or other antibacterials as long as they do not interfere with the stability or function of the N-halo- or N,N-dihaloamino acids of the invention.

The amounts or concentrations of N-halo- or N,N-dihaloamino acid in the compositions of the invention may vary over broad ranges. For example, a composition may contain from 0.001 to 100% by weight of the composition of the N-halo- or N,N-dihaloamino acid. In case of 100%, the composition may be applied in the form of a powder without any carrier substance. A typical range of the composition will include 0.1 to 95% by weight of the composition of the N-halo- or N,N-dihaloamino acid, for example, 0.1 to 50%, or 0.1 to 10%, for example, 0.5 to 5%. In solutions, usually a lower concentration of the N-halo- or N,N-dihaloamino acid will be applied. For example, a concentration of 1 to 2% may be appropriate in case of a rinse or spray. In another range, the concentration of the compound or its derivatives may be about 0.01% to about 20% of the composition by weight.

In case of nasopharyngeal application a catheter for nasal application containing a 0.5 to 5%, for example a 1% solution of the N-halo- or N,N-dihaloamino acid or its salt with a pH of 2-8, preferably 3.5 to 5 may be used for several weeks using about 5 to 50 ml, for example, 10 to 15 ml of the solution for each treatment. After each treatment the rinsing solution will be suctioned off.

The invention includes pharmaceutical compositions comprising (i) at least a halogenated compound and (ii) at least a N-halogenated or N,N-dihalogenated derivative of at least of a compound selected from amino acids described herein. More specifically, such compositions include a N-halogenated or N,N-dihalogenated derivative of formulae (I), (II), (IIA), (III), (IIIA), (IV) or a derivative thereof. In one aspect, the halogenated compound is an alkaline metal hypohalide, such as sodium hypochlorite, but more preferably a hypohalous acid, most preferably hypochlorous acid. These binary pharmaceutical compositions have anti-inflammatory, immuno-modulatory, bactericidal, antibacterial, anti-infective, antimicrobial, sporicidal, disinfectant, antifungal and antiviral effect and tissue healing stimulation without exhibiting substantial stimulation of myeloperoxidase activity in a mammal. The hypochlorite titer of these pharmaceutical compositions is below or equal to 1 mole/liter of available chlorine, particularly of a hypochlorite of an alkaline metal, especially sodium hypochlorite or hypochlorous acid. Its minimum titer is greater than or equal to about 1 picomole/liter. The N-chloramine or N,N-dichloroamine titer of these compositions is less than or equal to about 5 moles/liter with a minimum of 0.01 femtomoles/liter.

The binary compositions of the invention may be combined with excipients or carriers that are appropriate for a particular use. Suitable excipients or carriers are disclosed in the present application but can also be found by consulting textbooks, such as Remington. For liquid compositions water is a preferred excipients or carrier, although other non-oxidizable compatible carriers may also be used. Some aqueous compositions will contain osmotic (isotonic) purified water. Other compositions do not require osmotic balancing. The aqueous compositions may also contain diverse agents that are compatible with the halogenated compound and the N-halogenated or N,N-dihalogenated derivative of at least of a compound selected from amino acids described herein, as well as compatible with the use to which the composition will be put. If the compositions are destined for a pharmaceutical use and administration to humans or animals, the excipients or carriers must be pharmaceutically acceptable, such as substantially non-toxic and not interfere with the intended use of the pharmaceutical compositions. The skilled person will be aware that the characteristics of the composition can be varied or modified. Such modification can be effect with regard to stability, for example, by including stabilizers; with regard to pH by including pH adjusting agents, such as buffers, bases or acids; with regard to density by agents that influence density, for example diluents that reduce density or by density-increasing agents that that have a higher density than water; with regard to solubility by adding solubilizers; with regard to viscosity by adding agents that will affect viscosity, either by increasing it, for example by adding biocompatible polymers, or by reducing it by adding agents that have a low viscosity profile; with regard to coloring by adding compatible dyestuffs or coloring agents that are not oxidized by the binary halogenated components; with regard to wetting properties by adding appropriate surface-active agents or surfactants; with regard to olfactory or gustatory properties of the binary compositions by adding agents that display an attractive smell or flavor, for example to facilitate use of the compositions for certain uses or users.

The preparation of the binary composition depends on its form, whether it is in solid, liquid or gaseous form. Solid compositions may be in form of a powder, or gel. Semisolid compositions may be in form of an ointment or cream. Liquid compositions may be in form of a solution, emulsion or suspension or an oil. Gaseous compositions may be in form of an aerosol. Details for such preparations for pharmaceutical uses can be found in Remington; details for such preparations for consumer products can be found in "The Chemical Formulary", H. Bennett Ed., Chemical Publishing Company (1998), vol. XXXIV.

Specific Methods for Using the Compositions of the Invention

In one aspect, the compositions of the invention are administered or used topically.

The acidic solutions of the present invention may be used in treating a number of patients with deep wounds, which do not respond to usual medications and locally applied treatments. In one aspect, the present invention provides a method for the treatment of various medical conditions such as promoting wound healing, reduction of pathogens in open wounds, wound decontamination, ocular disinfection or decontamination, oral disinfection, antifungal therapy, ophthalmic applications, reduction of pathogens in pulmonary infections, reduction of pathogens in burns, lavage, reduction of infectious load in organs for transplantation, reduction of bacterial load in autologous or artificial tissue transplantation, oral disinfection antifungal therapy, treatment of biofilm for cystic fibrosis and related diseases, treatment of viral infections, treatment of skin diseases, and tissue repair and regeneration, which method comprises using the solution of the present invention by applying the solution to the site where treatment is required. Non-limiting examples of biofilm that may be treated using the solutions of the present invention include those cited in the review article entitled "*Is there a role for quorum signals in bacterial biofilms?*" by S. Kjelleberg, and S. Molin, PMID: 12057677 (PubMed-indexed for MEDLINE).

The solutions of the invention may be effective in reducing bacterial load thus improving wound healing. The solutions could be well tolerated, improve the granulation of wound tissue, reduce the need for debridement compared to prior art solutions with patients reporting less pain during their treatment and could potentially dampen the inflammatory response through cytokine regulations. See Mainnemare A, Megarbane B, Soueidan A, Daniel A, Chapple I L. Hypochlorous acid and taurine-N-monochloramine in periodontal diseases. *J Dent Res.* 2004 November; 83(11):823-31. Review.

Oral Care

The acidic solution of the invention may be used to treat canker sores (mouth ulcers) or cold sores by rinsing the affected area. For example, the solution can be used by soaking the cold sore 3-4 times a day, each time with 2-3 applications, and putting the solution in contact with the sore for 20-30 seconds. The solution may also be used as a mouth rinse for dental and mouth hygiene and to control infection. In this instance, the solution may be used as a gargling solution to fight throat infection. The solution may be applied with the help of a cotton swab for more specific areas. The solution can be used once or several times a day according to a patient's needs and condition.

Dental Equipment Care

The choice of specific cleaning or disinfecting agents of the invention is largely a matter of judgment, guided by product label claims and instructions and government regulations. A single liquid chemical composition might not satisfy all disinfection requirements in a given dental practice or facility. Realistic use of a liquid composition containing a N-halo- or N,N-dihalo amino acid, optionally in conjunction with an inorganic hypohalous compound, depends on consideration of multiple factors, including the degree of microbial killing required; the nature and composition of the surface, item, or device to be treated; and the cost, safety, and ease of use of the available agents. Selecting one appropriate product with a higher degree of potency to cover all situations might be more convenient.

In the United States, liquid chemical germicides (disinfectants) are regulated by EPA and FDA. In health-care settings, EPA regulates disinfectants that are used on environmental surfaces (housekeeping and clinical contact surfaces), and FDA regulates liquid chemical sterilants/high-level disinfectants used on critical and semicritical patient-care devices. Disinfectants intended for use on clinical contact surfaces (e.g., light handles, radiographic-ray heads, or drawer knobs) or housekeeping surfaces (e.g., floors, walls, or sinks) are regulated in interstate commerce by the Antimicrobials Division, Office of Pesticide Programs, EPA, under the authority of the Federal Insecticide, Fungicide, and Rodenticide Act (FIFRA) of 1947, as amended in 1996. Under FIFRA, any substance or mixture of substances intended to prevent, destroy, repel, or mitigate any pest, including microorganisms but excluding those in or on living man or animals, must be registered before sale or distribution. To obtain a registration, a manufacturer must submit specific data regarding the safety and the effectiveness of each product.

The formulations of the invention may be tested by using accepted methods for microbicidal activity, stability, and toxicity to animals and humans. These data must be submitted to EPA with proposed labeling. If EPA concludes the product may be used without causing unreasonable adverse effects, the product and its labeling are given an EPA registration number, and the manufacturer may then sell and distribute the product in the United States. FIFRA requires users of products to follow the labeling directions on each product explicitly. The following statement appears on all EPA-registered product labels under the Directions for Use heading: "It is a violation of federal law to use this product inconsistent with its labeling." This means that dental healthcare facilities must follow the safety precautions and use directions on the labeling of each registered product. Not following the specified dilution, contact time, method of application, or any other condition of use is considered misuse of the product.

FDA, under the authority of the 1976 Medical Devices Amendment to the Food, Drug, and Cosmetic Act, regulates chemical germicides if they are advertised and marketed for use on specific medical devices (e.g., dental unit waterline or flexible endoscope). A liquid chemical composition of the invention marketed for use on a specific device is considered, for regulatory purposes, a medical device itself when used to disinfect that specific medical device. Also, this FDA regulatory authority over a particular instrument or device dictates that the manufacturer is obligated to provide the user with adequate instructions for the safe and effective use of that device. These instructions must include methods to clean and disinfect or sterilize the item if it is to be marketed as a reusable medical device.

The Center for Disease Control CDC recommends disinfecting environmental surfaces or sterilizing or disinfecting medical equipment, and DHCP should use products approved by EPA and FDA unless no such products are available for use against certain microorganisms or sites. However, if no registered or approved products are available for a specific pathogen or use situation, DHCP are advised to follow the specific guidance regarding unregistered or unapproved (e.g., off-label) uses for various chemical germicides. For example, no antimicrobial products are registered for use specifically against certain emerging pathogens (e.g., Norwalk virus), potential terrorism agents (e.g., variola major or *Yersinia pestis*), or Creutzfeldt-Jakob disease agents.

One point of clarification is the difference in how EPA and FDA classify disinfectants. FDA adopted the same basic terminology and classification scheme as CDC to categorize medical devices (i.e., critical, semicritical, and non-critical) and to define antimicrobial potency for processing surfaces (i.e., sterilization, and high-, intermediate- and low-level disinfection). EPA registers environmental surface disinfectants based on the manufacturer's microbiological activity claims when registering its disinfectant. This difference has led to confusion on the part of users because the EPA does not use the terms intermediate- and low-level disinfectants as used in CDC guidelines.

Potency against *Mycobacterium tuberculosis* has been recognized as a substantial benchmark. However, the tuberculocidal claim is used only as a benchmark to measure germicidal potency. Tuberculosis is not transmitted via environmental surfaces but rather by the airborne route. Accordingly, use of such products on environmental surfaces plays no role in preventing the spread of tuberculosis. However, because mycobacteria have among the highest intrinsic levels of resistance among the vegetative bacteria, viruses, and fungi, a composition of the invention when designated with a tuberculocidal claim on the label is considered capable of inactivating a broad spectrum of pathogens, including such less-resistant organisms as bloodborne pathogens (e.g., HBV, HCV and HIV). It is this broad-spectrum capability, rather than the product's specific potency against mycobacteria, that is the basis for protocols and regulations dictating use of tuberculocidal chemicals for surface disinfection.

EPA also lists disinfectant products according to their labeled use against these organisms of interest as follows:
List B. Tuberculocide products effective against Mycobacterium species.
List C. Products effective against human HIV-1 virus.
List D. Products effective against human HIV-1 virus and HBV.
List E. Products effective against *Mycobacterium* species, human HIV-1 virus, and HBV.
List F. Products effective against HCV.

Microorganisms vary in their resistance to disinfection and sterilization, enabling CDC's designation of disinfectants as high-, intermediate-, and low-level, when compared with EPA's designated organism spectrum. However, exceptions to this general guide exist, and manufacturer's label claims and instructions should always be followed.

Dental Care and Hygiene

Periodontal disease is a general term used to describe diseases that effect the gingival and supporting tissue connected to bone and teeth in the jaw. See "Periodontal Disease", Ray Williams, New England Journal of Medicine 322: 373-382, 1990). Gingivitis (an early stage of the disease) and periodontitis are caused by specific bacteria and the host's reaction to the disease. For example, an increase in actinomyces and also the presence of *Fusibacterium nucleatum*, species of lactobacillus, veillonella and treponema has been implicated in causing gingivitis. Adult periodontitis is associated with *Bacteriodes gingivalis, B. intermedius, Actinimyces actinomycetemcomitans* and *B. forsythus*. A number of other species may also participate in active periodontal disease.

Commonly considered, antimicrobial therapy is the use of antibiotics to help fight periodontal (gum) disease which is caused by certain oral bacteria. Typically, antibiotics are used in conjunction with scaling and root planing. Some dentists use antimicrobial therapy only as a last resort, while others use it more frequently. In some cases, antimicrobial therapy can eliminate the periodontal disease. In others, periodontal surgery still is needed. However, the use of the compositions of this invention formulated for dental applications, referred herein as the "dental compositions", has the key advantage over the use of antibiotics that it does not induce antibiotic resistance, gastrointestinal discomfort or allergic effects.

Most people with periodontal disease do not receive antimicrobial therapy. This form of therapy generally is used for certain situations, including:

Necrotizing ulcerative gingivitis (NUG), a rare, aggressive form of periodontal disease that occurs mostly in people aged 15 to 35

Rapidly progressive periodontal disease

Periodontal disease that has not responded to other types of treatment

Patients who have weakened immune systems or other serious medical conditions.

However, because use of the dental compositions of the invention does not involve treatment with an antibiotic, the dental compositions of the invention can more frequently be used to control microbial infections or plaque (the collection of bacteria that accumulates on teeth) which may be the cause of dental caries. Although the mouth contains many different bacterial strains, only certain strains appear to cause dental decay. The dental compositions of the invention are effective against the large number of bacteria found in the mouth, in particular against acid-producing bacteria which are the ones that cause tooth decay, for example, *Streptococcus mutans*. The compositions of the invention are effective to control or prevent smooth surface decay, pit and fissure decay as well as decay in the enamel. In case a patient has especially active decay-causing bacteria in their mouth, the dentist may prescribe a mouth rinse which includes the dental compositions of the invention for several weeks to kill off the bacteria that cause tooth decay.

The dental compositions of the inventions are also useful for the co-treatment of pulpitis, a painful inflammation of the tooth pulp, for the treatment of a periapical abscess, which is a collection of pus or cellulitis originating from a bacterial infection. The dental compositions of the invention may be used in conjunction with antibiotics.

The dental compositions of the invention are also suitable for the treatment of periodontal diseases caused by accumulation of bacteria, such as gingivitis, herpetic gingivostomatitis caused by viral infection, gingivitis of pregnancy caused by hormonal changes, pericoronitis where the gum swells over a tooth that has not fully emerged or gingivitis of leukemia, or periodontitis, a type of gingivitis extending to the supporting structures of the tooth.

The dental compositions of the invention may be used in conjunction with professional dental hygiene performed, that is either during cleaning of the teeth or pockets using scaling, or after professional care, on patients by dental hygienists.

Before choosing the compositions of the present invention, a dentist may decide to take a sample of the bacteria and send it to a lab. The lab grows the bacteria, identifies them, and determines which concentration or formulation of the compositions of the invention would work best against them. The dentist or periodontist will then use this information to prescribe the dental composition that is most effective for the infection. However, because the dental compositions of the invention are so effective in killing the bacteria effecting dental diseases, this step often may be omitted.

Therapy for periodontal disease can be given systemically or locally. Local therapy is given in the dentist's chair, and involves placing the dental composition directly into the affected parts of the mouth. There are several types of local therapy, including:

Gel—The dentist injects a gel containing the compositions of the invention under the gums. The area is sealed and covered with a special bandage to prevent leakage. After seven to 10 days, the dentist removes the bandage and any remaining gel.

Chip—The dentist places a chip containing a dental composition containing the N-halo- or N,N-dihalo amino acids under your gums. The chip dissolves over seven to 10 days.

Powder—The dentist squirts a powder containing the compositions of the invention under the gums. The powder dissolves over a three-week period.

Ribbon—The dentist places a floss-like fiber under the gums that slowly releases N-halo- or N,N-dihalo amino acids. The ribbon is removed after about 10 days.

Microspheres—The compositions of the invention are formulated in compatible carrier materials as bioerodible or biodegradable microspheres, microparticles or microcapsules that are placed in the gum pocket and slowly release the compositions. The carrier polymer should be substantially resistant against the N-chloro or N,N-dihalo amino acids and dissolve over time. Examples of such polymers can be found in an article by J. C. Middleton, A. J. Tipton in *Medical Plastics and Biomaterials Magazine, March* 1998, p. 30.

Antimicrobial therapy usually lasts one to two weeks. Once the dentist has decided on using the composition comprising N-halo- or N,N-dihalo amino acids, for example, the patient first will undergo scaling and root planing. This procedure removes plaque and calculus (tartar) from under the gum line and smoothes any bumps or irregular areas on the tooth roots, where plaque can easily accumulate. After scaling and root planing, the dentist may prescribe some type of local antimicrobial therapy.

Aftercare

The dentist will recheck a patient after two or three months to see if the therapy is effective. If the disease does not respond to treatment with the composition comprising N-halo- or N,N-dihalo amino acids, the next step will depend on several factors, including the severity of the disease. The dentist can prescribe an antibiotic or schedule periodontal surgery. Some patients may receive several rounds of treatment of N-halo- or N,N-dihalo amino acids before their disease responds. Others need to be on long-term antibiotic therapy to keep their disease under control. Once a patient has undergone successful treatment for periodontal disease, it's important to help prevent recurrence. Impregnated dental floss may also be used after a visit with the dentist to provide continuous contact of the affected areas with the N-halo- or N,N-dihalo amino acids compositions. Maintenance therapy involves regular visits to the dentist or periodontist; this is usually every two to four months for people treated for periodontitis and every six months for people treated for gingivitis.

The dental compositions of the invention have the benefit that they avoid the risks of antibiotic therapy, such as antibiotic resistance or an allergic reaction to the antibiotic medication or adverse reactions (such as rash, hives or stomach upset). As with other types of infections, inappropriate use of antibiotics can lead to organisms becoming resistant to the effects of these medications. As part of preventive therapy the patient may use the compositions as a solution for oral rinse or direct application to gums (pockets) using an applicator.

Ophthalmic Care

The physiologically-balanced, acidic solution of the invention may be used in place of a saline solution to remove a foreign body from, to rinse, or to irrigate the eyes. It can also be applied topically before or after surgery to disinfect an eye and surrounding tissues. The solution can be used once or several times a day according to a patient's needs and condition. The solution can be applied by dropping it directly into the eyes as necessary. It can also be applied by soaking a gauze and applying the saturated gauze to the eyes for one or several minutes. It can also be used to clean the eyes by gently wiping the eyes with saturated gauze. The solution can also be poured into a small eye washer, then the washer is inverted over the eye and the eyelid opened and closed several times.

The physiologically-balanced, acidic solution of the invention may be used for the treatment of ocular disinfection or decontamination. In addition, it may be used as a replacement for silver nitrate in the disinfection of the eyes of neonates.

The solutions of the present invention may be used for the cleaning eyes in adults and in pediatrics. For example, various viral infections, bacterial or fungal infections, or pathogenic agents may be effectively treated with the solution of the present invention. Non-limiting examples of pathogenic agents that could be successfully treated with the solution of the present invention include Chlamydia trachomatis, gonorrhea as well as other bacterial, fungal, and viral infections. The compositions of the present invention may be used especially for pre- and post-operative disinfection.

The reader will see that the solution of the invention has applications in the treatment of many different types of wounds, including, without limitation, diabetic ulcers, gangrene, venous ulcers, decubitus ulcers, pressure ulcers, wounds due to bites, acute trauma wounds, surgical wounds and burns. The composition of the invention is also useful as an irrigation solution, for example, during dental, periodontal, and ophthalmic procedures. The composition of the invention can also be used for pre- and post-operative cleaning of tissue sites, and as a gargling solution for treatment of canker sores.

Methods of Using a Solution for Skin Disinfection:

The solution of the present invention may also be used to treat skin that is infected. In a skin of a patient showing medical signs of infection, the solution of the present invention may be applied directly to the area of the skin that is infected. After at least one application of the solution onto the infected skin using standard methods of application known in the art, the disinfective properties of the solution may be noted.

Reduction of Pathogens in Pulmonary Infections:

The solution of the present invention may be used for the reduction of pathogens in pulmonary infections. For example, various viral or bacterial and fungal infections may be effectively treated with the solution of the present invention. Non-limited examples of infections that may be effectively treated using the solution of the present invention include anthrax spores present in the lungs, and the reduction of pneumonia causing bacteria in the lungs, including strep bacteria and the like.

Methods of Using the Solutions of Invention in Gynecology:

The composition of the present invention may be used for the treatment of gynecological infections, such as urinary tract infections and the like. For example, various microorganisms, yeasts (e.g., *Monilia, Candida albicans*, etc), bacterial infections, HSV-2, HIV or other pathogenic agents may be effectively treated with the solution of the present invention. Optionally, the application of the solutions of the present invention can be used with other medications for the treatment of gynecological infections. For example, use as a lavage of birth canal in pregnant female patients with suspected venereal diseases, and potentially as bathing and cleansing solution on babies right after birth in the deliver rooms of hospitals or as disinfectant on catheters and shunt in dialysis room.

Method of Use as a Treatment for Topical Infections

The compounds of the current invention may be used to treat topical infections by incorporating them into creams, ointments or lotions for use in such conditions. Such creams, ointments or lotions might be used a broad variety of skin conditions and may incorporate penetration enhancers in order to deliver the antimicrobial activity of the compound to microbes present beneath the outer (epidermis) layers of the skin.

Method of Use to Prevent Surgical Site Infections

Isotonic solutions of the present invention may be used as an irrigant during surgery in order to prevent the development of surgical site infections, that frequently lead to prolonged hospitalizations and, occasionally, in death. The use of a solution of the present invention in place of saline could substantially reduce the risks of such infections especially in the case of gastric surgery and of prolonged operations, where the rate of infections may be as high as 10%.

Method of Use for Disinfection of Medical Devices and Surgical Implements

The solution of the present invention may be used for the reduction of pathogens on the surfaces of medical devices and surgical implements to prevent infection to the patient on whom the implements and devices are used, or in whom they are implanted. The solution may also be used for the reduction or elimination of infections that occur at the entry ports of catheters and shunts that are particularly prone to such infections.

Method of Use for Surface Disinfection

The solution of the present invention may be applied directly or through delivery from a device that creates a mist (aerosolization) to the surfaces of a room, vehicle interior or other such largely confined space in order to reduce or eliminate infectious pathogens that may be suspected to be present. In such an application, it could be used to decontaminate operating theaters where infectious pathogens have been detected or rooms, vehicles and other surfaces where biological warfare agents have been dispersed.

Method of Use for Improving Food Safety

The solution of the present invention may be used for reducing pathogens on food (including, without limitation, meats, fruits and vegetables). The solution could be applied as a wash or mist to the food, or the food could be dipped in the solution. Taurine would be major residual product of such application and taurine is an essential nutrient that is considered to be safe in human food.

The solution of the present invention may also be applied to surfaces and implements used in the preparation of foods to prevent the transfer of pathogens from such surfaces and implements to the food.

Method of Use as an Antimicrobial Preservative

The compounds of the present invention may be used as a means of ensuring that microbes cannot survive in solutions intended for use in injection, infusion or for use in the eye by incorporation of an appropriate amount of such compound into the solution at the time of manufacture.

Method of Use as an Antimicrobial

The solution of the present invention may be used as a means of safely and rapidly disinfecting the hands of surgeons and nurses to reduce the risk of transporting infectious agents into an operating theatre. Additionally, solution of the present invention may be used to eliminate the infectious agent from the skin of patients (pre and post operative) in the area of a surgical incision.

Method of Wound Care

Patients suffering from long-lasting non-healing wounds should be treated with the acidic composition of the present invention on a daily basis, typically about once or twice a day.

The solution of the invention may be used as follows: a gauze material or gauze pad is presoaked with enough solution to saturate it and is then squeezed to remove excess solution. This removes species present in the gauze which would react with and reduce the effectiveness of the solution of the invention. The gauze is wetted after this procedure, but not soaked. Additional solution is then applied to completely wet the gauze, which is then immediately applied to the wound. In the alternative, the gauze may be applied to the wound and then additional solution is applied. Typically the wound site is packed with the solution-soaked gauze, and optionally, a Vaseline gauze can be applied on top of the packed wound to keep it moist and free of contaminating germs. The wound site is then wrapped with wound dressings as is standard in the art. The solution may also be used to clean a wound by pouring it directly on the wound site to remove any necrotic tissue by a mechanical procedure, and also as a cleanser or irrigant.

The patient may also make use of a "wound care kit" provided by NovaCal which permits the patient to periodically pour the solution of the present invention onto the wound site without having to remove the dressing. This kit provides ease-of-use, portability and dramatically reduces exposure of the wound to/from re-infection. The wound care kit includes a package containing the solution of the invention and bandaging material. Often the kit contains a package containing the solution of the invention and a specialized bandage for use in combination with the solution. The specialized bandage keeps the skin surrounding the wound dry while the wound is treated. Further, the bandage may be applied in a physician's office or at a hospital, with the patient continuing care at home; may be applied and used at home under the instructions of a physician; or for minor injuries, the wound care kit may be used as an "over the counter" treatment by the patient alone.

Packaging for Certain Uses

In another aspect of the invention, the solutions of the present invention may be packaged to contain the solution in individual, single use containers. The single-use containers may be used for example, for application in single change of dressing or equivalents thereof. The single-use containers of the present invention may be used in conjunction with commonly used bandages. In another aspect of the invention, a wound care kit may comprise single-use containers of the solutions of the present invention with the specialized bandages for various applications.

In another aspect of the invention, the solutions of the present invention may be produced in-situ by the use a dual-chamber apparatus or packaging as shown in FIG. 1 with or without a third mixing chamber.

Figure 1:
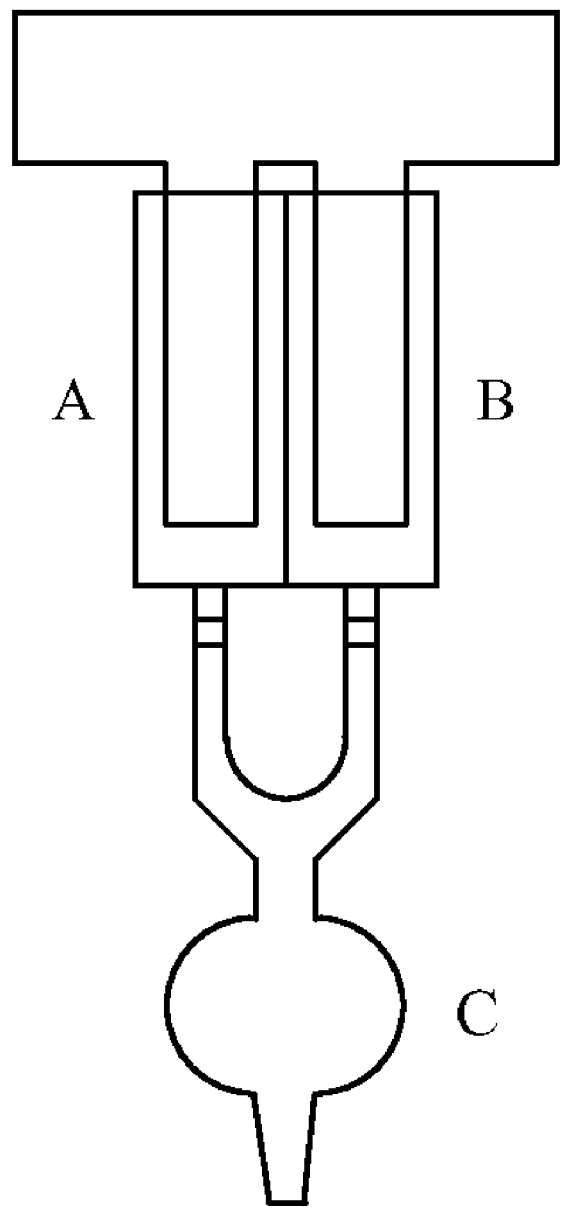
FIG. 1: A dual chamber apparatus for the preparation of NNDCT on site.

The Dual-Chamber may consist of two syringes or pouches. To make NNDCT solution with a concentration of 3.2 mM at pH 3.5, for example, chamber A is filled with 12.8 mM NaOCl solution, chamber B is filled with 3.3 mM taurine dissolved in acidified 1.8% of saline solution. The acidity of the solution in chamber B is adjusted with 1 M HCl so that when the solutions in two chambers are mixed either in a common delivery tube or in a mixing chamber C, the reaction will give desired NNDCT concentration and pH value. Since Taurine is stable in acidic solution, and NaOCl is stable at room temperature, the use of the on-site preparation method described above can avoid the stability problem of NNDCT solution.

Aspects of the Invention

In one aspect of the invention, there is provided a pharmaceutical composition comprising an N,N-dihaloamino acid of the formula (I)

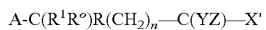

$$A\text{-}C(R^1R^\circ)R(CH_2)_n\text{-}C(YZ)\text{-}X'$$

or a derivative thereof; wherein A is hydrogen, HalHN— or Hal$_2$N—; Hal is halogen selected from the group consisting of fluoro, chloro, bromo and iodo; but chloro, bromo and iodo are preferred; R is a carbon carbon single bond or a divalent cycloalkylene radical with three to six carbon atoms; $R^1$ is hydrogen, lower alkyl or the group —COOH; $R^\circ$ is hydrogen or lower alkyl; or $R^1$ and $R^\circ$ together with the carbon atom to which they attach form a ($C_3$-$C_6$)cycloalkyl ring; n is 0 or an integer from 1 to 13; Y is hydrogen, lower alkyl, —NH$_2$ or —NHal$_2$; Z is hydrogen or lower alkyl; and X' is hydrogen, —COOH, —CONH$_2$, —SO$_3$H, —SO$_2$NH$_2$, —P(=O)(OH)$_2$ or —B(OH)$_2$; if R is a divalent cycloalkylene radical n is 0 or an integer up to and including 11, the divalent radical R or divalent radical —(CH$_2$)$_n$— being optionally substituted with —NHHal or —NHal$_2$; the derivative being a pharmaceutically acceptable salt, ester with lower alkanols, or lower alkanoyl derivative of the —NH$_2$ group attached to the carbon atom to which the substituent X' is attached.

In another aspect, $R^\circ$ is lower alkyl. In another aspect, R is a carbon carbon single bond and n is 0 or an integer from 1 to 7. In yet another aspect, n is 0 or an integer from 1 to 5. In one variation of the above aspects, n is 0 or an integer from 1 to 3.

In another aspect, there is provided the composition wherein the N-halo- or N,N-dihaloamino acid comprises 1 or 2 —NHHal or —NHal$_2$ groups, or wherein the N-halo- or N,N-dihaloamino acid comprises 1 —NHHal or —NHal$_2$ group. In one variation of the above, the —NHHal or —NHal$_2$ group is in the alpha, beta or gamma position to the group X'. In another aspect, A is —NHHal or —NHal$_2$. In yet another aspect, the —NHHal or —NHal$_2$ group is attached to the divalent radicals R or —(CH$_2$)$_n$—. In another aspect of the above, Hal is chloro.

In one aspect of the invention, the derivative is a pharmaceutically acceptable salt.

In another aspect, there is provided a composition having a concentration of the N-halo- or N,N-dihaloamino acid or its derivative is between 0.1 to 100 mM and a pH range between about 3 to about 4.8, 3.0 to 4.5, or 3.5 to 4.5, or at about 3.5. In another aspect, the concentration of the N-halo- or N,N-dihaloamino acid or its derivative may be between 0.01 mM to 1 M.

In another aspect of the invention, there is provided a composition with bactericidal, antibacterial, anti-infective, antimicrobial, sporicidal, disinfectant, antifungal and antiviral activity comprising an N,N-dihalo-amino acid of the formula (II)

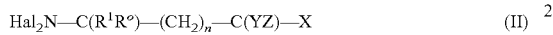

$$Hal_2N—C(R^1R^o)—(CH_2)_n—C(YZ)—X \quad (II)$$

or wherein the Hal$_2$N— group is replaced with the HalHN— group [formula(IIA)], or a derivative thereof; wherein Hal is halogen selected from the group consisting of fluoro, chloro, bromo and iodo; R$^1$ is hydrogen, lower alkyl or the group —COOH; R$^o$ is hydrogen or lower alkyl; or R$^1$ and R$^o$ together with the carbon atom to which they attach form a (C$_3$-C$_6$) cycloalkyl ring; n is 0 or an integer from 1 to 3; Y is hydrogen, lower alkyl or —NH$_2$;

Z is hydrogen or lower alkyl; and X is —COOH, —CONH$_2$, —SO$_3$H or —SO$_2$NH$_2$; the derivative being selected from the group consisting of pharmaceutically acceptable salts, esters with lower alkanols, and lower alkanoyl derivatives of the —NH$_2$ group attached to the carbon atom to which the substituent X is attached; and a pharmaceutically acceptable carrier; the composition having a concentration of the N,N-dihaloamino acid or its derivative between 0.1 to 100 mM and a pH range between about 3 to about 4.8, 3.0 to 4.5, or 3.5 to 4.5, or at about 3.5. In one variation of the above, the composition having a concentration of the N,N-dihaloamino acid or its derivative between 0.01 mM to 1 M. In another variation, the pH of the composition is about 2 to about 7.

In yet another aspect, there is provided a stabilized composition with bactericidal, antibacterial, anti-infective, antimicrobial, sporicidal, disinfectant, antifungal and antiviral activity comprising an N,N-dihalo-amino acid of the formula (II)

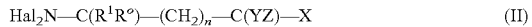

$$Hal_2N—C(R^1R^o)—(CH_2)_n—C(YZ)—X \quad (II)$$

or wherein the Hal$_2$N— group is replaced with the HalHN— group [formula(IIA)], or a derivative thereof; wherein Hal is halogen selected from the group consisting of fluoro, chloro, bromo and iodo; R$^1$ is hydrogen, lower alkyl or the group —COOH; R$^o$ is hydrogen or lower alkyl; or R$^1$ and R$^o$ together with the carbon atom to which they attach form a (C$_3$-C$_6$) cycloalkyl ring; n is 0 or an integer from 1 to 3; Y is hydrogen, lower alkyl or —NH$_2$; Z is hydrogen or lower alkyl; and X is —COOH, —CONH$_2$, —SO$_3$H or —SO$_2$NH$_2$; the derivative being selected from the group consisting of pharmaceutically acceptable salts, esters with lower alkanols, and lower alkanoyl derivatives of the —NH$_2$ group attached to the carbon atom to which the substituent X is attached; and a pharmaceutically acceptable carrier; the composition having a concentration of the N-haloamino acids or N,N-dihaloamino acid or its derivative between 0.1 to 50 mM and a pH range between about 2 to about 7, 3 to 6, 3 to 4.8, 3 to 4.5, or 3.5 to 4.5, or at about 3.5. In one variation, the composition having a concentration of the N-haloamino acids or N,N-dihaloamino acid or its derivative is between 0.01 mM to 1 M.

In one aspect of the above, the composition is in a receptacle ensuring its long-term stability required by its bactericidal, antibacterial, anti-infective, antimicrobial, sporicidal, disinfectant, antifungal or antiviral use. That is, the compositions disclosed herein may be stored in a receptacle ensuring its long-term stability and shelf life sufficient for its application as a bactericidal, antibacterial, anti-infective, antimicrobial, sporicidal, disinfectant, antifungal or antiviral agent.

In yet another aspect, there is provided a composition comprising an N,N-dihalo-amino acid of the formula (II)

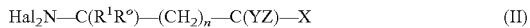

$$Hal_2N—C(R^1R^o)—(CH_2)_n—C(YZ)—X \quad (II)$$

or wherein the Hal$_2$N— group is replaced with the HalHN— group [formula(IIA)], or a derivative thereof; wherein Hal is halogen selected from the group consisting of fluoro, chloro, bromo and iodo; R$^1$ is hydrogen, lower alkyl or the group —COOH; R$^o$ is hydrogen or lower alkyl; or R$^1$ and R$^o$ together with the carbon atom to which they attach form a (C$_3$-C$_6$) cycloalkyl ring; n is 0 or an integer from 1 to 3; Y is hydrogen, lower alkyl or —NH$_2$; Z is hydrogen or lower alkyl; and X is —COOH, —CONH$_2$, —SO$_3$H or —SO$_2$NH$_2$; the derivative being selected from the group consisting of pharmaceutically acceptable salts, esters with lower alkanols, and lower alkanoyl derivatives of the —NH$_2$ group attached to the carbon atom to which the substituent X is attached; and a pharmaceutically acceptable carrier; the composition having a pH range between about 2 to about 7, 3 to 6, 3 to 5, or at about 3.5, and the compositions having bactericidal, antibacterial, anti-infective, antimicrobial, sporicidal, disinfectant, antifungal and antiviral activity. In one variation, the concentration of the N-haloamino acid or the N,N-dihaloamino acid or its derivative between 0.01 mM to 1 M, or between 0.1 to 100 mM, preferably 0.3 to 50 mM. In another aspect, the composition is in stabilized form. In yet another aspect, the composition is stored in a receptacle ensuring its long-term stability required by its bactericidal, antibacterial, anti-infective, antimicrobial, sporicidal, disinfectant, antifungal or antiviral use.

In one aspect of the invention, there is provided a composition comprising an N,N-dihalo-amino acid of the formula (II)

$$Hal_2N—C(R^1R^o)—(CH_2)n—C(YZ)—X \quad (II)$$

or wherein the Hal$_2$N— group is replaced with the HalHN— group [formula(IIA)], or a derivative thereof; wherein Hal is halogen selected from the group consisting of fluoro, chloro, bromo and iodo; R$^1$ is hydrogen, lower alkyl or the group —COOH; R$^o$ is hydrogen or lower alkyl; or R$^1$ and R$^o$ together with the carbon atom to which they attach form a (C$_3$-C$_6$) cycloalkyl ring; n is 0 or an integer from 1 to 3; Y is hydrogen, lower alkyl or —NH$_2$; Z is hydrogen or lower alkyl; and X is —COOH, —CONH$_2$, —SO$_3$H or —SO$_2$NH$_2$; the derivative being selected from the group consisting of pharmaceutically acceptable salts, esters with lower alkanols, and lower alkanoyl derivatives of the —NH$_2$ group attached to the carbon atom to which the substituent X is attached; and a pharmaceutically acceptable carrier; the composition having a pH range between about 2 to about 7, 3 to 6, 3 to 5, or at about 3.5 in the preparation of a medicament for bactericidal, antibacterial, anti-infective, antimicrobial, sporicidal, disinfectant, antifungal and antiviral use.

In another variation, the composition has a concentration of the N-haloamino acid or the N,N-dihaloamino acid or its derivative between 0.01 mM to about 1 M, 0.1 to 100 mM, or 0.3 to 50 mM. In another variation, the medicament is in a receptacle ensuring its long-term stability required by its bactericidal, antibacterial, anti-infective, antimicrobial, sporicidal, disinfectant, antifungal or antiviral use.

In one variation, there is provided a method of preventing or treating an infection caused by a bacterial, a microbial, a sporal, a fungal or a viral activity in a mammal, the method comprising the administration of a bactericidal, antibacterial, anti-infective, antimicrobial, sporicidal, disinfectant, antifungal and antiviral amount of an N,N-dihalo-amino acid of the formula (II)

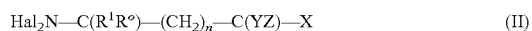

$$\text{Hal}_2\text{N}—\text{C}(\text{R}^1\text{R}^o)—(\text{CH}_2)_n—\text{C}(\text{YZ})—\text{X} \qquad (\text{II})$$

or wherein the $Hal_2N$— group is replaced with the HalHN— group [formula(IIA)]

or a derivative thereof; wherein Hal is halogen selected from the group consisting of fluoro, chloro, bromo and iodo; $R^1$ is hydrogen, lower alkyl or the group —COOH; $R^o$ is hydrogen or lower alkyl; or $R^1$ and $R^o$ together with the carbon atom to which they attach form a ($C_3$-$C_6$)cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; the derivative being selected from the group consisting of pharmaceutically acceptable salts, esters with lower alkanols, and lower alkanoyl derivatives of the —$NH_2$ group attached to the carbon atom to which the substituent X is attached; and a pharmaceutically acceptable carrier. In another variation, the composition has a pH range between about 2 to about 7, 3 to 6, 3 to 5, or at about 3.5. In another aspect, the composition has a concentration of the N-haloamino acid or the N,N-dihaloamino acid or its derivative between 0.01 mM to about 1 M, 0.1 to 100 mM, or 0.3 to 50 mM. In yet another aspect of the invention, the composition is in stabilized form.

In another aspect of the invention, the composition being in a receptacle ensuring its long-term stability required by its bactericidal, antibacterial, anti-infective, antimicrobial, sporicidal, disinfectant, antifungal or antiviral use. In one aspect, the composition is isotonic and physiologically balanced.

In another aspect, the composition has a therapeutic index of about 1000 to about 5,000, defined by the ratio of its $IC_{50}$ at one hour against both L929 mouse lung epithelial cells and primary human fibroblasts to its Minimum Bactericidal Concentration against *Escherichia coli* at one hour.

In one aspect, there is provided a composition with bactericidal, antibacterial, anti-infective, antimicrobial, disinfectant, antifungal and sporicidal and antiviral activity comprising an N,N-dihalo-amino acid of the formula (IV)

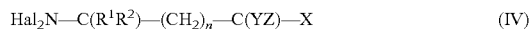

$$\text{Hal}_2\text{N}—\text{C}(\text{R}^1\text{R}^2)—(\text{CH}_2)_n—\text{C}(\text{YZ})—\text{X} \qquad (\text{IV})$$

or a derivative thereof; wherein Hal is halogen selected from the group consisting of fluoro, chloro, bromo and iodo; $R^1$ is hydrogen, lower alkyl or the group —COOH; $R^2$ is lower alkyl; or $R^1$ and $R^2$ together with the carbon atom to which they attach form a ($C_3$-$C_6$)cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; the derivative being selected from the group consisting of pharmaceutically acceptable salts, esters with lower alkanols, and lower alkanoyl derivatives of the —$NH_2$ group attached to the carbon atom to which the substituent X is attached. In one variation of the formula IV, the group $Hal_2N$ is replaced with a HalNH— group. In one variation, $R^1$ is hydrogen, or lower alkyl; n is 0, 1 or 2; Y is hydrogen or lower alkyl; Z is hydrogen or lower alkyl; and X is —$SO_3H$ or —$SO_2NH_2$; or a derivative thereof; the derivative being selected from the group consisting of pharmaceutically acceptable salts or esters with lower alkanols. In another variation, Y and Z are both hydrogen; X is —$SO_3H$; the derivative being selected from the group consisting of pharmaceutically acceptable salts. In another aspect of the above, the composition comprises a pharmaceutically acceptable carrier.

In one aspect of the above composition, the pH range is between about 2 to about 7, 3 to 6, 3 to 5, or about 3.5. In another aspect of the above, the composition is isotonic and physiologically balanced.

In one aspect of the invention, the N,N-dihaloamino acid is a member selected from the group consisting of N,N-dichloro-2,2-dimethyltaurine; N-chloro-2,2-dimethyltaurine; N,N-dichloro-1,1,2,2-tetramethyltaurine; N-chloro-1,1,2,2-tetramethyltaurine; N,N-dibromo-2,2-dimethyltaurine; N-bromo-2,2-dimethyltaurine; N,N-dibromo-1,1,2,2-tetramethyltaurine; N-bromo-1,1,2,2-tetramethyltaurine; N,N-diiodotaurine; N-iodotaurine; N,N-dichloro-2-methyltaurine; N-chloro-2-methyltaurine; N,N-dichloro-2,2,3,3-tetramethyl-β-alanine; N-chloro-2,2,3,3-tetramethyl-β-alanine; N,N-dichloro-3,3-dimethylhomotaurine; N-chloro-3,3-dimethylhomotaurine; N,N-dichloro-2-methyl-2-aminoethanesulfonic acid; N-chloro-2-methyl-2-aminoethanesulfonic acid; N,N-dichloro-1-methyl-2-aminoethanesulfonic acid, N-chloro aminotrimethylene phosphonic acid; N,N-dibromo 2-amino-5-phosphonopantanoic acid; N-bromo 2-amino-5-phosphono-pentanoic acid; N,N-dichloro aminoethylphosphonic acid diesters, such as the diethylester; N-chloro aminoethylphosphonic acid diesters, such as the diethylester; N,N-dichloro-1-amino-1-methylethane phosphonic acid; N-chloro 1-amino-1-methylethane phosphonic acid; N,N-dichloro-1-amino-2-methylethane phosphonic acid; N-chloro 1-amino-2-methylethane phosphonic acid; N,N-dichloro-1-amino-2-methylpropane phosphonic acid; N-chloro-1-amino-2-methylpropane phosphonic acid; N,N-dichloro leucine phosphonic acid; N-chloro leucine phosphonic acid; N,N-dichloro 4-amino-4-phosphono-butyric acid; N-chloro-4- amino-4-phosphonobutyric acid; (±) N,N-dichloro-2-amino-5-phosphonovaleric acid; (±) N-chloro -2-amino-5-phosphonovaleric acid; N,N-dichloro (+)2-amino-5-phosphonovaleric acid; N-chloro (+)2-amino-5-phosphonovaleric acid; N,N-dichloro d,1-2-amino-3-phosphonopropionic acid; N-chloro d,1-2-amino-3-phosphono-propionic acid; N,N-dichloro-2-amino-8-phosphonooctanoic acid; N-chloro-2-amino-8-phosphonooctanoic acid; N,N-dichloro leucine boronic acid; N-chloroleucine boronic acid, N,N-dichloro-β-alanine boronic acid; N-chloro-β-alanine boronic acid; or a derivative thereof; the derivative is selected from the group consisting of pharmaceutically acceptable salts and esters with lower alkanols.

In yet another aspect of the invention, there is provided a method for controlling or preventing the growth of bacteria, microbes, spores, fungi or viruses or the proliferation of infections and the source of infections, the method comprising the application of an effective amount of a composition of the present invention to an area, space or material requiring the control or prevention of growth or proliferation. In one variation, the pH of the composition is between about 2 to about 7, 3.0 to 6.8, 3 to 6, 3 to 5, or about 3.5.

In one aspect of the above methods, the N,N-dihalo amino acid or derivative thereof is prepared in situ. In one variation of the above methods, the material to be treated is selected from the class consisting of food, animal feed, surgical instruments, surgical equipment, medical devices and equipment used for such purposes.

In one aspect, the invention provides an N,N-dihaloamino acid of the formula (IV)

or a derivative thereof; wherein Hal is halogen selected from the group consisting of fluoro, chloro, bromo and iodo; $R^1$ is hydrogen, lower alkyl or the group —COOH; $R^2$ is lower alkyl; or $R^1$ and $R^2$ together with the carbon atom to which they attach form a $(C_3-C_6)$cycloalkyl ring; n is 0 or an integer from 1 to 3; Y is hydrogen, lower alkyl or —$NH_2$; Z is hydrogen or lower alkyl; and X is —COOH, —$CONH_2$, —$SO_3H$ or —$SO_2NH_2$; the derivative being selected from the group consisting of pharmaceutically acceptable salts, esters with lower alkanols, and lower alkanoyl derivatives of the —$NH_2$ group attached to the carbon atom to which the substituent X is attached. In one variation of the N,N-dihaloamino acid, $R^1$ is hydrogen, or lower alkyl; n is 0, 1 or 2; Y is hydrogen or lower alkyl; Z is hydrogen or lower alkyl; and X is —$SO_3H$ or —$SO_2NH_2$; or a derivative thereof; the derivative being selected from the group consisting of pharmaceutically acceptable salts or esters with lower alkanols. In another variation, Y and Z are hydrogen; X is —$SO_3H$; the derivative being selected from the group consisting of pharmaceutically acceptable salts.

In one aspect of the invention, the composition is selected from the group consisting of N,N-dichloro-2,2-dimethyltaurine; N,N-dichloro-1,1,2,2-tetramethyltaurine; N,N-dibromo-2,2-dimethyltaurine; N,N-dibromo-1,1,2,2-tetramethyltaurine; N,N-dichloro-2- methyltaurine; N,N-dichloro-2,2,3,3-tetramethyl-β-alanine; N,N-dichloro-3,3-dimethylhomotaurine; and N,N-dichloro-1-methyl-2-aminoethanesulfonic acid or a pharmaceutically acceptable salt thereof.

In one variation of the N,N-dihaloamino acid, Hal is chloro, or a pharmaceutically acceptable salt thereof.

In another aspect, there is provided a pharmaceutical composition comprising an N,N-dihalo amino acid of the invention, or a derivative thereof.

In yet another aspect, there is provided a method of preventing or treating an infection caused by a bacterial, a microbial, a sporal, a fungal or a viral activity in a mammal, the method comprising the administration of a bactericidal, antibacterial, anti-infective, antimicrobial, sporicidal, disinfectant, antifungal and antiviral amount of an N-halo- or N,N-dihalo-amino acid of the invention.

In another variation, the invention provides a method for controlling or preventing the growth of bacteria, microbes, spores, fungi or viruses or the proliferation of infections and the source of infections, the method comprising the application of an effective amount of the N-halo- or N,N-dihalo amino acid above to an area, space or material requiring the control or prevention of growth or proliferation.

In one variation, the composition has a concentration of the N-halo- or N,N-dihaloamino acid or its derivative between 0.01 mM to about 1 M, 0.1 and 100 mM or 0.3 to 50 mM and a pH range between about 3 to about 4.8, 3.0 to 4.5, or 3.5 to 4.5, or at about 3.5.

In another aspect, the composition is in stabilized form, the composition having a concentration of the N-halo- or N,N-dihaloamino acid or its derivative between 0.1 and 100 mM or 0.1 to 50 mM and a pH range between about 2 to about 7, 3 to 6, 3 to 4.8, 3 to 4.5, 3.5 to 4.5, or at about 3.5. The pH may be adjusted using suitable buffer systems well-known to a person skilled in the art. In one variation the composition being in a receptacle ensuring its long-term stability required by its bactericidal, antibacterial, anti-infective, antimicrobial, sporicidal, disinfectant, antifungal or antiviral use.

In one aspect of the invention, there is provided the use of an N-halo- or N,N-dihalo-amino acid of the invention in the preparation of a bactericidal, antibacterial, anti-infective, antimicrobial, sporicidal, disinfectant, antifungal and antiviral activity composition. In another aspect, there is provided a composition as described above, further comprising a halogenated compound selected from the group consisting of a hypohalous acid or a salt thereof. In one variation of the above, the composition is acidic.

In a particular variation of the method described above, the method further comprising the use of a halogenated compound selected from the group consisting of a hypohalous acid or a salt thereof. In one variation of the above method, the administered composition is acidic.

Various methods may be developed for preparing the compounds of the present invention. Representative methods for preparing these compounds are provided in the Examples. However, the compounds of the present invention may also be synthesized by other synthetic routes as is well known in the art of synthetic chemistry. Some of the present compounds have chiral centers. The preparation of the compounds of the present invention may result in the formation of mixtures of different stereoisomers (enantiomers, diastereomers). Unless a particular stereochemistry is specified, recitation of a compound is intended to encompass all of the different possible stereoisomers. The compounds of the present invention can also be prepared as a pharmaceutically acceptable acid addition salt by reacting the free base form of the compound with a pharmaceutically acceptable inorganic or organic acid. The base addition salts may also be prepared by reacting the acid with a pharmaceutically acceptable inorganic or organic base.

EXAMPLE 1

Method of Preparation

Reagents: All solutions were made with deionized, or Millipore water. NaOCl (6%) solution was purchased from VWR. Taurine was purchased from Sigma. NaCl and HCl are reagent-grade.

Synthesis and Characterization of N,N-dichlorotaurine (NNDCT)

In this study, NNDCT was prepared by dissolving taurine powder in HOCl solution (pH 3.5) at a HOCl/Taurine ratio of 2.

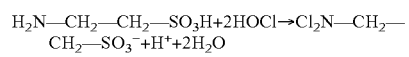

To make 1 liter of 1.6 mM of NNDCT in 0.9% NaCl solution at pH 3.5, add 8.6 g of NaCl into a 1000-ml volumetric flask, then add 500 ml Millipore water into the flask to dissolve the salt. Add 2 ml of 1 M HCl into the NaCl solution, followed by adding 22 ml of 0.158 M NaOCl. Mix the solution. Then add 0.267 g of taurine into the flask and fill the volumetric flask up to the mark with Millipore water. Stir the solution for 5 minutes.

NNDCT has a maximum absorbance at 300 nm with a molar absorptivity of 370 $M^{-1}cm^{-1}$. When $OCl^-$ solution (pH 9.5) was added into the taurine solution, N-Chlorotaurine (NCT) ($ClHN-CH_2-CH_2-SO_3^-$) was the only product formed.

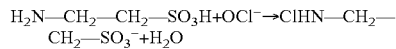

$$H_2N-CH_2-CH_2-SO_3H+OCl^- \rightarrow ClHN-CH_2-CH_2-SO_3^- +H_2O$$

NNDCT and NCT are spectrophotometrically distinguishable. NCT has a maximum absorbance at 252 nm. The yield of NNDCT was calculated from its absorbance at 300 nm. This preparation method gives a yield of 91% of NNDCT. Iodometric titration gives a $I_2$/NNDCT ratio of 2. This suggests that NNDCT retains the two oxidizing equivalents of HOCl. Both chlorine moieties in NNDCT are able to oxidize the $I^-$ to $I_2$. NNDCT decomposes in solution, but it is more stable at low temperature. A stability study on NNDCT solution (pH 3.5) was performed at three temperatures, 4° C., room temperature and 40° C. The solution was sealed in ampoules. The stability of NNDCT at three temperatures is in the following order: 4° C.>room temperature>40° C. In 4 weeks, 5.4% of NNDCT is lost when stored in refrigerator (4° C.) ($[NNDCT]_{initial}$=1.47 mM).

N,N-dichlorotaurine is very soluble in water at a pH range from 1 to 10. N,N-dichlorotaurine can be identified and quantitatively determined by UV spectroscopy. N,N-dichlorotaurine has a maximum UV absorbance at 300 nm and a molar absorptivity of 370 $M^{-1}cm^{-1}$.

NNDCT is not volatile. A solution of 1.47 mM in 0.9% saline at pH 3.5 was filled in two glass bottles. One bottle was capped tightly and another was capped loosely. There was no difference in the concentration of NNDCT in two bottles after 4 weeks at room temperature.

Isolation of the pure powder form of NNDCT and storage under inert atmosphere provides a more stable source for NNDCT. Additionally, reformulation of the solid matrix of NNDCT in a pill format assists in the stabilization of NNDCT. This pill formulation has been selected to prevent decomposition while providing ease of use in the intended pharmaceutical application (contact lens disinfections, other application).

EXAMPLE 2

Antimicrobial Activity

Bactericidal Activity:

To determine the bactericidal activity, we used Escherichia coli (ATCC 11229). The bacterial culture was diluted in sterile saline to prepare inocula. Various test articles were transferred to individual tubes already containing $1.0 \times 10^5$ to $2.0 \times 10^5$ Colony Forming Units (CFU)/mL bacteria and mixed by gentle vortexing and then incubated at 37° C. for 1 or 24 hours. In an attempt to mimic as far as possible the conditions, which could be produced in vivo if the test articles were used as antiseptics, bacterial plating in a Petri dish was performed immediately after the designated exposure time without the addition of a neutralizer, and independently with addition of neutralizer (as control). Thus, 0.1 mL was removed after 1 or 24 hours exposure times and plated. Plates were incubated at 37° C., and the numbers of bacteria were counted by direct colony count to numerate the surviving bacteria as CFU/mL. Positive growth controls were made with sterile 0.9% saline. All test articles were tested three times. The results were tabulated to show the comparison of antimicrobial effectiveness range of HOCl, $OCl^-$, NNDCT and 0.9% saline at various pH levels. At pH 3.5 NNDCT showed an effective antimicrobial concentration range between 0.0149 to 1.49 mM at 60 min, and an effective antimicrobial concentration range between 0.000149 to 1.49 mM at 24 hrs, whereas the effective antimicrobial concentration range for HOCl commenced at 0.016 at 60 min and at 0.0016 mM at 24 hrs. At pH 3.5 NNDCT was better or as effective against E. coli as HOCl.

In these studies for the first time we have demonstrated (in parallel) the bactericidal and cell toxicity profiles of N-Chloramines as compared to various test articles. Both N-Chlorotaurine (NCT) and N,N-Dichlorotaurine (NNDCT) were synthesized in 0.9% physiological concentration of NaCl with controlled pH according to procedures described above. These solutions were tested for their physicochemical properties before analyzing their biological activities. Diluted solutions of NCT and NNDCT are colorless and isotonic and display exceptionally rapid antimicrobial activity. Production of these oxidants appears to be pH-dependent. NCT is formed exclusively in alkaline pH, whereas NNDCT is formed in acidic pH.

Comparative antimicrobial assays using NNDCT in the solution of the present invention at pH 5.0 and 3.5 and NCT at pH 9.5 demonstrated a bacterial (E. coli) killing efficiency of about 300 fold greater for NNDCT at pH 3.5 over NNDCT at pH 5.0 and 1000 fold higher killing efficiency of NNDCT at pH 3.5 as compared to NCT at pH 9.5 within the 60 min exposure time at 37° C. (Table-1).

TABLE 1

Product summary:

| Product | Color | pH | Tonicity | Physical Status | MBC (µg/mL) |
|---------|-------|-----|----------|-----------------|-------------|
| NCT | clear | 9.5 | Isotonic | solution | 142.5 |
| NNDCT | clear | 5.0 | Isotonic | solution | 38.0 |
| NNDCT | clear | 3.5 | Isotonic | solution | 0.136 |

MBC is the Minimum Bactericidal Concentration

The antimicrobial activity and killing time not only were concentration dependent but also increased markedly by lowering the pH. NCT is less antimicrobial than NNDCT on an equal concentration basis by a factor of 1000 fold.

EXAMPLE 3

Cytotoxicity Assay:

Cytotoxicity was assessed by a colorimetric assay system, initially described by Scudiero et al., using 3'-(phenylaminocarbonyl)-3,4-tetrazolium-bis (4-methoxy-6-nitro) benzene sulfonic acid hydrate (XTT), ProCheck™ cell viability assay (Evaluation of a soluble tetrazolium/formazan assay for cell growth and drug sensitivity in culture using human and other tumor cell lines described by Scudiero D A, Shoemaker R A H, Paul K D, Monks A, Tierney S, Nofziger T H, Currens M J, Seniff D, Boyd M R. Cancer Res. 1988 Septmeber 1;48 (17):4827-33). Similar approaches for determining the cell viability are used by other investigators. Three cell types were used: mouse lung epithelial cells (L929), primary human skin fibroblast and primary human keratinocyte cells cultured in Dulbecco Modified Eagle's Medium and Keratinocyte defined medium with corresponding growth factors plus antibiotics. Cells were trypsinized and counted under the microscope and seeded at 1000-to-2000 cells per well of a flat-bottom 96-well plate. Cells were allowed to grow over-night at 37° C. Next day, tissue culture media was removed and cells were rinsed with fresh media 1× and then left in 50 µL of tissue culture media. Test articles were prepared as 2-fold dilutions and 200 µL was added into each set of 4-wells (total volume per well=250 µL). Cells were exposed to test articles for 60 min at room temperature. Immediately after the exposed time, test article from each well was removed and cells were fed with 250 µL of fresh media. Plates were incubated at 37° C. for 18-20 hours. The following day media was removed again and replaced with 100 µL/well of fresh media containing 10/100 µL XTT-reagent. Cells were incubated under growth conditions (5% $CO_2$ at 37° C. humidified incubator), protected from light, until color development was achieved. Absorbance was read at 450 nm with reference wavelength at 750 nm using Molecular Device ThermoMax Plate reader, blanking the plate on the medium-only assay blank wells. Untreated cells receiving XTT reagents-only served as positive cell proliferation control.

When cell inhibitory concentration toxicity index ($CCI_{50}$) was determined (measured as 50% of cells still alive), $CCI_{50}$ of NNDCT was at 7 mM and showed a substantially higher cell viability of Primary Human Skin Fibroblasts in the XTT Assay than for $CI_{50}$ of HOCl ($IC_{50}$=0.8 mM), betadine ($IC_{50}$=0.01 mM) or $OCl^-$ ($IC_{50}$=0.66 mM). Similar results were attained in the XTT Assay performed on mouse lung epithelial cells (L929) where more than 90% viability for NNDCT was observed at a concentration of 7 mM versus substantially less than 50% viability for $OCl^-$ at concentrations of 0.6 mM and betadine at concentrations of 0.02 mM.

Cytotoxicity and Therapeutic Index

NNDCT has been subjected to rigorous in vitro safety testing using United States Pharmacopoeia's standard cell assay (mouse lung epithelial cells, L929), as well as primary human skin cells. We discovered that NNDCT has a very low cell toxicity index in both cell types: Primary human fibroblast and L929 cells as compared to other antiseptic test articles: HOCl and Povidone-Iodine (see below). Unlike Povidone Iodine where cell toxicity was a major concern, NNDCT demonstrated to be cell compatible with a much safer toxicity profile. In fact, the therapeutic index (TI), which is defined as the ratio of a concentration tolerated by the assayed cells (in vitro cytotoxicity or $IC_{50}$) over the Minimum Bactericidal Concentration (MBC) for NNDCT was about 5,000 as compared to about 300 and 7 for HOCl and Povidone-Iodine, respectively (Table 2).

TABLE 2

Summary of Minimum Bactericidal Concentration (MBC) and Therapeutic Index data

| Product | pH | $MBC^a$ (µg/mL) | $IC_{50}$ (µg/mL) | $T.I^b$. on $HF^c$ |
|---|---|---|---|---|
| NNDCT | 3.5 | 0.29 | 1442 | 4972 |
| HOCl | 3.5 | 0.16 | 47 | 297 |
| Povidone-Iodine | 4.2 | 0.38 | 2.5 | 7 |

$^a$Minimum Bactericidal Concentration (MBC) for *Escherichia coli* (ATCC11229)
$^b$Therapeutic Index and $^c$Primary human skin fibroblast cells.

Application of NNDCT as safer topical disinfectant particularly in ophthalmic, chronic non-healing wounds and burn patients could be a great advantage, because use of other disinfectants with major toxic side effects is highly discouraged by healthcare authorities. Since food safety is also a major health issue, the application of NNDCT as a broad disinfectant can be extended to food industry.

EXAMPLE 4

Preparation of 2-Amino-2-Methylpropanesulfonic Acid:

2-Amino-2-methyl-1-propanol (Aldrich, 5.0 g, 56 mmol, 1.0 equiv.) was taken in DCM (100 ml), BOC anhydride (14.6 g, 67 mmol, 1.2 equiv.) was added portion wise at 0° C. and the mixture was stirred over night at rt. The solution was allowed to warm up slowly overnight without the ice bath being removed. Solvent was removed by rotoevaporation. EtOAc (50 ml) was added followed by water (50 ml). The organic layer was separated and washed one more time with water and brine, and then dried ($Na_2SO_4$) and concentrated to give 12 g of the crude product.

To a solution of the BOC protected amino alcohol (10.0 g, 52.5 mmol, 1.0 equiv.) in DCM (100 ml) was added triethylamine (TEA, 11 mL, 7.5 mmol, 1.5 equiv.). The reaction mixture was cooled to 0° C. and a solution of methanesulfonyl chloride (4.4 mL, 58 mmol, 1.1. equiv.) in DCM (40 ml) was added dropwise. The mixture was allowed to warm up to room temperature and stirred for 30 min. No starting material was observed by TLC. Water was added and the DCM was separated. The organic layer was washed with water, saturated solution of sodium bicarbonate, and brine. The organic layer was then dried ($MgSO_4$) and concentrated to give 12.6 g. of crude product, which was purified by flash chromatography to give 6.35 g clean product.

The purified BOC-aminosulfonate obtained from above (6.35 g., 23.7 mmol, 1.0 equiv.) was added to a RB flask, and 30 ml of HCl 4N in dioxane (30 mL, 118.5 mmol, 5 equiv.) was added. After over night stirring at room temperature, no starting material was observed by tlc. Solvent was removed by rotoevaporation, and DCM (10 ml) was added, and then evaporated. The white solid was placed under vacuum for 30 min. and used for the next step without further purification.

Sodium sulfite (4.25 g, 33.7 mmol, 1.5 equiv.) was dissolved in 33 ml water (1M solution) and added to the starting amine hydrochloride intermediate (4.6 g, 22.5 mmol, 1.0 equiv.) at room temperature. After overnight stirring, precipitates were collected and washed several times with methanol to give 4.2 g of a white solid. This material was dissolved in water and ethanol was added and left at room temperature for 6 hrs. Precipitates were collected and the mother liquor was evaporated to give 2.2 g white solid which was washed with water (2×5 ml) and left under vacuum to give 1.2 g of the desired, pure product as the sodium salt. The desired product was identified by elemental analysis.

N-Monohalo amino acids of the invention may be also prepared as described in the literature: X. L. Armesto, M. Canle L., M. V. Garcia and J. A. Santaballa *Chemical Society Reviews*, 1998, volume 27, 453; Juan M. Antelo, Florencio Arce, Paula Calvo, Juan Crugeiras and Ana Ríos *J. Chem. Soc., Perkin Trans.* 2, 2000, (10), 2109-2114; J. M. Antelo; F. Arce, J. Crugeiras, M. Parajó *Journal of Physical Organic Chemistry*, Volume 10, Issue 8, Pages 631-636.

EXAMPLE 5

As an example, the procedure for the preparation of 2-(dichloroamino)-2-methylpropanesulfonic acid (also referred to herein as N,N-dichloro-2,2-dimethyltaurine) is described as follows:

Step 1: Synthesis of 2-amino-2-methylpropanesulfonic acid (Braghiroli, D.; Bella, M. D. Tetrahedron Letters, 1996, 37, 7319-7322).

2-amino-2-methylpropanesulfonic acid is prepared by reduction of 2-hydroxyisobutyronitrile (acetone cyanohydrin) to 1-amino-2-methyl-2-propanol, followed by protection with $(Boc)_2O$. After mesylation and removal of the protecting group, the hydrochloride obtained is allowed to react with sodium sulfite to give 2-amino-2-methylpropanesulfonic acid.

Step 2: Chlorination of 2-amino-2-methylpropanesulfonic acid

To make 1liter of 1.6 mM of 2-(dichloroamino)-2-methylpropanesulfonic acid in 0.9% NaCl solution at pH 3.5, add 8.6 g of NaCl into a 1000-ml volumetric flask, then add 500 ml Millipore water into the flask to dissolve the salt. Add 2 ml of 1 M HCl into the NaCl solution, followed by adding 22 ml of 0.158 M NaOCl. Mix the solution. Then add 0.355 g of 1,1-dimethylethanesulphonic acid into the flask and fill the volumetric flask up to the mark with Millipore water. Stir the solution until the reaction is completed as indicated for example by UV or NMR. We have also prepared N,N-chlorinated ornithine, N,N-dichloro homotaurine and N,N-dichloro alanine. All these dichloro compounds have very similar UV spectra (λmax=~300 nm) and molar absorptivities.

Into an acidic HOCl solution, a stoichiometric amount of amino acid or their salt (powder) is added (the molar ratio of HOCl : amino acid=2:1). Then the mixture solution is stirred for about 15 minutes. The pH of the resulting solution is lower than the pH of the starting HOCl solution. The product is identified and the completion of the reaction is followed by an Uv-vis spectrophotometer. The pH of the solution is adjusted with hydrochloric acid or sodium hydroxide solution to the desired pH value. The concentration of the solution is determined on UV spectrophotometer by using the corresponding molar absorptivity at the $\lambda_{max}$. A more detailed procedure is described in the following example.

EXAMPLE 6

Preparing 1 liter of 0.05 M of Dichloro Homotaurine solution

Step 1. Prepare 1 liter of 0.1 M HOCl solution with a pH<5.
Step 2. Add 8.06 g of sodium homotaurine (sodium 3-amino-1-propansulfonic, MW=161.13) into the HOCl solution in step 1. Stir the solution for about 15 minutes.
Step 3. Take an aliquot of solution in step 2 and make 100-fold dilution. Take the UV spectrum of the diluted solution to identify the product, which has $\lambda_{max}$ at 303 nm (see the attached table).
Step 4. Adjust the pH of the solution resulted in step 2 to the desired pH with NaOH or HCl.
Step 5. Repeat the procedure in step 3 to measure the concentration of the dichloro homotaurine (the molar absorptivity is 329.0 $M^{-1}cm^{-1}$, see table below).

TABLE

Molar Absorptivities of N,N-Dichloro- and N,N-dibromo-Amino Acid Compounds

| Compounds | $\lambda_{max}$ (nm) | $\epsilon$ ($M^{-1}cm^{-1}$) |
|---|---|---|
| N,N-dichloro taurine | 302 | 332.9[a] |
| N,N-dichloro homotaurine | 303 | 329.0[c] |
| N,N-dichloro β-alanine | 301 | 327.6[c] |
| N,N,N',N'-tetrachloro ornithine | 300[c,d] | 241[c,d] |
| N,N-dibromo taurine | 241 | 2713[b], 2708[c] |

[a]Gottardi, W.; Nagl, M. Arch. Pharm. Pharm. Med. Chem. 2002, 9, 411-421.
[b]Thomas, E.; Bozeman, P.; Jefferson, M.; King, C. J. Bio. Chem. 1995, 7, 2906-2913.
[c]Determined in this study.
[d]Based on a 4:1 molar ratio of chlorinating agent to ornithine.

EXAMPLE 7

The results of our discovery provide support for antimicrobial activity of NNDCT in 0.9% saline at pH 3.5. These antimicrobial activities were determined to be considerable in a AM range and increased significantly by increasing the concentration and or exposure time. In contrast, cell toxicity was seen at a 1000-fold higher range in the mM range. We showed that NNDCT treated cells were able to tolerated the treatment and be able to go through normal cell proliferation cycles as compared to untreated control cells in our XTT assay.

EXAMPLE 8

NNDCT solutions with a concentration of 1.49 mM at pH 3.0, 3.5, 4.0, and 5.0 were prepared. The spectra and the concentrations of the solutions were measured on the UV-vis spectrometer. The results showed that the spectrum and the concentration of NNDCT solution did not change in the pH range from 3.0 to 5.0.

Preparation

Add 8.8 g NaCl, 2 ml of 1.0 M HCl, and 0.278 g of taurine into a 1000-ml volumetric flask, followed by adding about 800 ml of deionized water into the flask. Shake the flask to dissolve NaCl and taurine powders. Then add 22 ml of 0.15M of the NaOCl solution into the flask. Fill the flask up to the mark with deionized water. Stir the solution with a magnetic stirring bar for 5 minutes. The concentration and the pH of the resulting solution were measured on a UV-vis spectrometer and a freshly calibrated Beckman pH meter. This solution has a concentration of 1.49 mM and a pH value of 3.85. 100 ml of NNDCT solution above (pH=3.85) was pipetted into a 250-ml beaker, 0.09 ml of 1.0 M HCl solution was added to this solution and stir. The final pH of this solution is 3.0. 100 ml of NNDCT solution with pH 3.85 solution was pipetted into a 250-ml beaker, 0.003 ml of 5.0 M NaOH solution was added to this solution and stir. The final pH of this solution is 4.85.

Solutions with varying pH values were prepared in a similar manner within the pH range of 3 to 5. All solutions show stability if properly stored as shown by their UV spectra.

General Procedure for Preparing the Monohalo-Amino Acid Compounds:

The amino acid or the salt of the amino acid (powder) is added into a basic $OX^-$(X=Cl, Br) solution (pH>8) or an $OX^-$(X=Cl, Br) solution in a phosphate buffer, such as a pH 7.4, at a molar ratio of $OX^-$:amino acid=1:1. The mixture solution is stirred for about 15 minutes. The product is identified and the completion of the reaction is followed by an UV-vis spectrophotometer. The pH of the solution is adjusted with hydrochloric acid or sodium hydroxide solution to the desired pH value. The concentration of the solution is determined on UV spectrophotometer by using the corresponding molar absorptivity at the $\lambda_{max}$. A more detailed procedure is described in the following example.

EXAMPLE 9

Preparation of a 1 liter of 0.05 M of Monochloro Homotaurine solution

Step 1: Prepare 1 liter of 0.05 M NaOCl solution with a pH>8.
Step 2: Add 8.06 g of sodium homotaurine (sodium 3-amino-1-propansulfonic, MW=161.13) into the NaOCl solution in step 1. Stir the solution for about 15 minutes.
Step 3: Take an aliquot of solution in step 2 and make 100-fold dilution. Take the UV spectrum of the diluted solution to identify the product, which has $\lambda_{max}$ at 252 nm (see the table below).
Step 4: Adjust the pH of the solution resulted in step 2 to the desired pH with NaOH or HCl.

EXAMPLE 10

The Synergistic Antiviral Effect of a 1:1 Mixture of Isotonic Hypochlorous Acid and N,N-Dichloro-1,1-dimethylethanesulphonic acid An equal volume of human adenovirus type 5 (Ad5, McEwen strain) was mixed with each of the three samples listed below. The mixtures were incubated at 37C for 1 hr and then diluted in tissue culture medium (Dulbecco's Modified Eagle Medium [DMEM] containing heat inactivated 2% fetal bovine serum). The mixtures were then diluted in 10-fold serial dilutions using the same diluent mentioned above. 0.1 ml of each diluted mixture was inoculated on to a A549 cell monolayer grown in 12 well plates (cell source, ATTC) and allowed to adsorb for 1 hr. The inoculum was removed and the monolayer rinsed with diluent and agarose/DMEM overlay applied. The plates were incubated at 37° C. in 5% CO2 atmosphere for 6 days. The monolayers were then fixed, stained and the plaques counted.

| Sample | Solution | undiluted $10^{-0}$ | Effect on monolayer | | | | | |
|---|---|---|---|---|---|---|---|---|
| | | | $10^{-1}$ | $10^{-2}$ | $10^{-3}$ | $10^{-4}$ | $10^{-5}$ | $10^{-6}$ |
| Ad5 control | Adenovirus control | DESTR | DESTR | DESTR | DESTR | TNTC | 37 | 7 |
| 1 | 37.5 mM NNDCDMES, pH 3.5 isotonic | Early toxic reaction to inoculum | 28 | 17 | 3 | 3 | 3 | 9 |
| 2 | 0.1% HOCl, pH 3.5 isotonic | 14 | 9 | 3 | 1 | 4 | 4 | 1 |
| 3 | 1:1 isotonic mixture of 37.5 mM NNDCDMES with 0.1% HOCl | Poor or bad monolayer | 0 | 0 | 0 | 1 | 1 | 0 |
| Saline control | 0.9% sterile saline | DESTR | DESTR | DESTR | DESTR | TNTC | 21 | 6 |

Abbreviations:
NNDCDMES: N,N-dichloro-1,1-dimethylethanesulphonic acid
DESTR: Monolayer destroyed
TNTC: Plaques too numerous to count Step 5: Repeat the procedure in step 3 to measure the concentration of the monochloro homotaurine (the molar absorptivity is 386 $M^{-1}cm^{-1}$, see table below).

TABLE

| Molar Absorptivities of Monochloro-Amino Acid Compounds | | |
|---|---|---|
| Compounds | $\lambda_{max}$ (nm) | $\epsilon$ ($M^{-1}cm^{-1}$) |
| N-Monochloro taurine | 252 | 415[a] |
| N-Monochloro homotaurine | 252 | 386[b] |
| N-Monochloro β-Alanine | 251 | 385[b] |

[a]Thomas E L.; Grisham M B, Jefferson M M. Meth. Enzymol. 1986, 132, 669-71.
[b]Determined in this study.

Following the above procedure and selecting the appropriate amino acid starting materials, the following N-halo amino acids may be prepared: N-chloro-2,2-dimethyltaurine, N-chloro-1,1,2,2-tetramethyltaurine, etc. (See the non-exclusive, representative list of compounds in paragraph [0054]).

The result for Sample 3 shows upon dilution that a 1:1 isotonic mixture of N,N-dichloro-1,1-dimethylethanesulphonic acid and hypochlorous acid has synergistic antiviral effect against Adenovirus, when compared with hypochlorous acid (Sample 2) or N,N-dichloro-1,1-dimethylethanesulphonic acid (Sample 1) alone.

EXAMPLE 11

Solution for Wound Treatment

HOCl (2 mM)
N,N-Dichloro-2,2-dimethyltaurine (20 mM)
NaCl (0.9%)
Water (100 ml)

What is claimed is:
1. A composition comprising an N-haloamino acid of the formula (I))

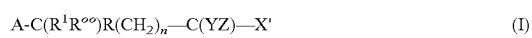

or a derivative or pharmaceutical composition thereof;
wherein A is HalHN—;

Hal is halogen selected from the group consisting of chloro and bromo;

R is a carbon-carbon single bond or a divalent cycloalkylene radical with three to six carbon atoms;

$R^1$ is lower alkyl or the group —COOH;

$R^o$ is lower alkyl; or $R^1$ and $R^o$ together with the carbon atom to which they attach form a ($C_3$-$C_6$)cycloalkyl ring;

n is 0 or an integer from 1 to 13;

Y is hydrogen, lower alkyl, —$NH_2$, —NHHal or —$NHal_2$;

Z is hydrogen or lower alkyl; and

X' is $SO_3H$;

if R is a divalent cycloalkylene radical n is 0 or an integer up to and including 11, the divalent cycloalkylene radical R or divalent radical —$(CH_2)_n$— being optionally substituted with —NHHal or —$NHal_2$;

the derivative being a pharmaceutically acceptable salt, ester with lower alkanols, or lower alkanoyl derivative of the —$NH_2$ group attached to the carbon atom to which the substituent X' is attached.

2. The composition of claim 1, wherein R is a carbon-carbon single bond and n is 0 or an integer from 1 to 7.

3. The composition of claim 1 wherein the —NHHal group is in the alpha, beta, or gamma position to the group X'.

4. The composition of claim 1 wherein the —NHHal group is attached to the divalent radical R or —$(CH_2)_n$—.

5. The composition of claim 1 wherein Hal is chloro.

6. The composition of claim 1 further comprising a solvent, wherein the concentration of the N-haloamino acid or its derivative is between 0.01 mM to 1 M and the composition has a pH of 2 to 7.

7. The composition of claim 6 wherein the pH is 3.5 to 4.5.

8. The composition of claim 1 further comprising a solvent, wherein the concentration of the N-haloamino acid or its derivative is about 0.01% to 20% of the composition by weight.

9. A composition of claim 1 with bactericidal, antibacterial, antimicrobial, germicidal, sporicidal, disinfectant, antifungal and antiviral activity.

10. A stabilized composition of claim 1.

11. The composition of claim 1, wherein the composition is stored in a receptacle ensuring its long-term stability and shelf life sufficient for its application as a bactericidal, antibacterial, antimicrobial, sporicidal, disinfectant, antifungal or antiviral agent.

12. A method of treating an infection caused by a bacterial, a microbial, a sporal, a fungal or a viral activity in a mammal, the method comprising the administration of an effective amount of a compound of claim 1.

13. The composition of claim 1, wherein the composition is isotonic and physiologically balanced.

14. The composition of claim 1 having a therapeutic index of 1000 to 5,000, defined by the ratio of its $IC_{50}$ at one hour against both L929 mouse lung epithelial cells and primary human fibroblasts to its Minimum Bactericidal Concentration against *Escherichia coli* at one hour.

15. An N-haloamino acid selected from the group consisting of N-chloro-2,2-dimethyltaurine; N-chloro-1,1,2,2-tetramethyltaurine; N-bromo-2,2-dimethyltaurine; N-bromo-1,1,2,2-tetramethyltaurine; N-chloro-3,3-dimethylhomotaurine; and pharmaceutically acceptable salts and esters thereof.

16. A method for controlling the growth of bacteria, microbes, spores, fungi or viruses, the method comprising the application of an effective amount of a composition of claim 1 to an area, space or material.

17. The method of claim 16, wherein the material to be treated is selected from the class consisting of food, animal feed, surgical instruments, surgical equipment, medical devices and equipment used for such purposes.

18. An N-haloamino acid of the formula (IV)

$$A'-C(R^1R^2)-(CH_2)_n-C(YZ)-X \qquad (IV)$$

or a derivative thereof; wherein

A' is the —NHHal group;

Hal is halogen selected from the group consisting of chloro and bromo;

$R^1$ is lower alkyl or the group —COOH;

$R^2$ is lower alkyl; or $R^1$ and $R^2$ together with the carbon atom to which they attach form a ($C_3$-$C_6$)cycloalkyl ring;

n is 0 or an integer from 1 to 3;

Y is hydrogen, lower alkyl or —$NH_2$;

Z is hydrogen or lower alkyl; and

X is —$SO_3H$;

the derivative being selected from the group consisting of pharmaceutically acceptable salts, esters with lower alkanols, and lower alkanoyl derivatives of the —$NH_2$ group attached to the carbon atom to which the substituent X is attached.

19. The N-haloamino acid of claim 18, wherein $R^1$ is lower alkyl;

n is 0, 1 or 2;

Y is hydrogen or lower alkyl;

Z is hydrogen or lower alkyl; and

X is —$SO_3H$;

or a derivative thereof; the derivative being selected from the group consisting of pharmaceutically acceptable salts.

20. The N-haloamino acid of claim 19, wherein Y and Z are hydrogen, the derivative being selected from the group consisting of pharmaceutically acceptable salts.

21. The composition of claim 1, further comprising a halogenated compound selected from the group consisting of a hypohalous acid or a salt thereof.

22. The composition of claim 5, further comprising a halogenated compound selected from the group consisting of a hypohalous acid or a salt thereof.

23. The composition of claim 21 wherein the composition is acidic.

24. The composition of claim 22 wherein the composition is acidic.

25. A product prepared from the reaction of an amino acid of the formula I with a halogen source under reaction conditions which lead to the replacement of one or two hydrogen atoms at the amino group of the amino acid, wherein formula I is $$A-C(R^1R^o)R(CH_2)_n-C(YZ)-X' \qquad (I)$$

or a derivative thereof;

wherein A is $H_2N$—;

R is a carbon-carbon single bond or a divalent cycloalkylene radical with three to six carbon atoms;

$R^1$ is lower alkyl or the group —COOH;

$R^o$ is lower alkyl; or $R^1$ and $R^o$ together with the carbon atom to which they attach form a ($C_3$-$C_6$)cycloalkyl ring, n is 0 or an integer from 1 to 13;

Y is hydrogen, lower alkyl, —$NH_2$;

Z is hydrogen or lower alkyl; and

X' is —$SO_3H$;

if R is a divalent cycloalkylene radical, n is 0 or an integer up to and including 11, the divalent cycloalkylene radical R or divalent radical —$(CH_2)_n$— being optionally substituted with —NHHal;

the derivative being a pharmaceutically acceptable salt, ester with lower alkanols, or lower alkanoyl derivative of the —$NH_2$ group attached to the carbon atom to which the substituent X' is attached.

26. The product of claim 25, wherein the halogen source is selected from the group consisting of HOCl or its salt, N-haloarylsulfonamide salts, $HClO_2$, N-chlorosuccinimide, N-bromosuccinimide, N-iodosuccinimide, $Cl_2$, $Br_2$, $I_2$, thionyl chloride, phosgene, $PCl_3$, $PCl_5$ and chlorinating agents.

* * * * *